United States Patent
Lancaster et al.

(10) Patent No.: US 9,487,748 B2
(45) Date of Patent: Nov. 8, 2016

(54) DUAL-COMPARTMENT BIOREACTOR FOR USE IN WASTEWATER TREATMENT AND ALGAL PRODUCTION

(71) Applicant: Palo Alto Research Center Incorporated, Palo Alto, CA (US)

(72) Inventors: Cory Lancaster, Palo Alto, CA (US); Francisco E. Torres, San Jose, CA (US); Mark J. Stephenson, Pleasanton, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 14/533,426

(22) Filed: Nov. 5, 2014

(65) Prior Publication Data

US 2016/0122705 A1    May 5, 2016

(51) Int. Cl.
| | |
|---|---|
| *C12M 1/00* | (2006.01) |
| *C12M 3/00* | (2006.01) |
| *C12N 1/12* | (2006.01) |
| *C02F 3/02* | (2006.01) |
| *C02F 3/32* | (2006.01) |
| *C12M 1/26* | (2006.01) |
| *C12M 1/04* | (2006.01) |
| *C02F 3/20* | (2006.01) |

(Continued)

(52) U.S. Cl.
CPC ............... *C12N 1/12* (2013.01); *C02F 3/025* (2013.01); *C02F 3/208* (2013.01); *C02F 3/301* (2013.01); *C02F 3/325* (2013.01); *C12M 21/02* (2013.01); *C12M 23/24* (2013.01); *C12M 33/14* (2013.01); *C12M 43/00* (2013.01); *C02F 3/006* (2013.01); *C02F 2203/004* (2013.01); *C02F 2203/006* (2013.01); *C02F 2209/22* (2013.01); *C02F 2305/06* (2013.01)

(58) Field of Classification Search
CPC ............ C12N 1/12; C02F 3/025; C02F 3/30; C02F 3/325; C02F 2203/004; C02F 2203/006; C02F 9/00; C02F 11/00; C02F 3/02; C02F 3/28; C02F 3/301; C02F 3/32; C02F 3/34; C12M 21/02; C12M 33/14; C12Q 1/02; Y02W 30/04; Y02W 30/43; Y02W 10/10; Y02W 10/15; Y02W 10/20; Y02W 10/23; Y02W 10/27
USPC ....................................................... 435/292.1
See application file for complete search history.

(56) References Cited

U.S. PATENT DOCUMENTS

| | | | |
|---|---|---|---|
| 5,254,143 A | * | 10/1993 | Anazawa ............... C12M 29/16 95/46 |
| 7,674,517 B2 | | 3/2010 | Ramsey et al. |

(Continued)

OTHER PUBLICATIONS

Hoffmann, Wastewater Treatment With Suspended and Nonsuspended Algae, Inireview, 1998, pp. 757-763, Department of Botany and Agricultural Biochemistry, University of Vermont, Burlington, VT 05405.

(Continued)

*Primary Examiner* — Nathan Bowers
(74) *Attorney, Agent, or Firm* — Fay Sharpe LLP

(57) ABSTRACT

A dual compartment bioreactor system includes a heterotrophic bioreactor, an autotrophic bioreactor, and a membrane between the autotrophic bioreactor and the heterotrophic bioreactor. The autotrophic bioreactor includes a transparent outer wall. Each population benefits from the products of the metabolism of the other. Methods for wastewater treatment and algal production utilize the system.

19 Claims, 18 Drawing Sheets

(51) Int. Cl.
*C02F 3/30* (2006.01)
*C02F 3/00* (2006.01)

(56) References Cited

U.S. PATENT DOCUMENTS

| | | | | |
|---|---|---|---|---|
| 2002/0168758 | A1* | 11/2002 | Martinez | C12M 23/34 435/297.4 |
| 2005/0242026 | A1* | 11/2005 | Morris | C02F 3/302 210/610 |
| 2007/0227970 | A1* | 10/2007 | Wickham | C02F 3/302 210/605 |
| 2008/0220523 | A1* | 9/2008 | Antwiler | C12M 25/10 435/394 |
| 2010/0200496 | A1* | 8/2010 | Graveleau | C02F 1/24 210/605 |
| 2010/0311157 | A1* | 12/2010 | Van Alstyne | C12M 23/00 435/294.1 |
| 2011/0053257 | A1* | 3/2011 | Ragsdale | C12M 23/04 435/292.1 |
| 2011/0151547 | A1* | 6/2011 | Bloch | C02F 3/02 435/292.1 |
| 2014/0302483 | A1* | 10/2014 | Kauling | C12N 5/0087 435/2 |

OTHER PUBLICATIONS

Wang et al., Cultivation of Green Algae *Chlorella* sp., In Different Wastewaters from Municipal Wastewater Treatment Plant, 2009, Appl Biochem Biotechnol, Springer Science+Business Media LLC, Humana Press, pp. 1-13.
Pittman et al., The potential of sustainable algal biofuel production using wastewater resources, Bioresource Technology, (2010), pp. 1-9, www.elsevier.com/locate/biortech.
Cai et al., Nutrient recovery from wastewater streams by microalgae: Status and prospects, Renewable and Sustainable Energy Reviews 19 (2013), pp. 360-369, www.elsevier.com/locate/rser.
Chojnacka et al., Kinetic and Stoichiometric Relationships of the Energy and Carbon Metabolism in the Culture of Microalgae, ISSN 1682-2978, Biotechnology, 3 (1): pp. 21-34, 2004, Asian Network for Scientific Information.
De-Bashan et al., Immobilized microalgae for removing pollutants: Review of practical aspects, Bioresource Technology, pp. 1611-1627, Environmental Microbiology Group, Northwestern Center for Biological Research (CIBNOR), La Paz, BCS, Mexico, The Bashan Foundation, Corvallis, OR, USA. www.elsevier.com/locate/biortech.
Aziz et al., Feasibility of Wastewater Treatment Using the Activated-Algae Process, Bioresource Technology 40 (1992), pp. 205-208, Department of Civil Engineering, Hydraulic and Environmental Engineering Division, National University of Singapore, Kent Ridge, Singapore 0511.
Sialve et al., Anaerobic digestion of microalgae as a necessary step to make microalgal biodiesel sustainable, Research Review Paper published in "Biotechnology Advances 27, 4 (2009), pp. 409-416".
McCarty et al., Domestic Wastewater Treatment as a Net Energy Producer-Can This be Achieved?, Environmental Science & Technology, Jul. 12, 2011, pp. 7100-7106, American Chemical Society 2011, ACS Publications, pubs.acs.org/est.
Udman et al., Dewatering of microalgal cultures: A major bottleneck to algae-based fuels, Journal of Renewable and Sustainable Energy 2, 012701 (2010), pp. 012701-1-012701-15, American Institute of Physics.
Moreno-Grau et al., A Mathematical model for waste water stabilization ponds with macrophytes and microphytes, Ecological Modelling 21 (1996), pp. 77-103, Elsevier.
Rodolfi, et al., Microalgae for Oil: Strain Selection, Induction of Lipid Synthesis and Outdoor Mass Cultivation in a Low-Cost Photobioreactor, Biotechnology and Bioengineering, vol. 102, No. 1, Jan. 1, 2009, pp. 100-112, 2008 Wiley Periodicals, Inc.

Schoener et al., Energy positive domestic wastewater treatment: the roles of anaerobic and phototrophic technologies, Environmental Science Process & Impacts, 2014, 16, pp. 1204-1222, Royal Society of Chemistry.
Li et al., Towards sustainable wastewater treatment by using microbial fuel cells-centered technologies, Environmental Science Process & Impacts, 2014, 7, pp. 911-924, Royal Society of Chemistry.
Porex, Porex TMF 4-Tubular Membrane Filter (TMF) Modules, www.porexfiltration.com, 2011, 2 pages.
Mohamed et al., Heterotropic Cultivation of Microalgae for Production of Biodiesel, Recent Patents on Biotechnology 2011, vol. 5, No. 2, pp. 1-13, Bentham Science Publishers Ltd.
Perez-Garcia et al., Heterotropic cultures of microalgae: Metabolism and potential products, ScienceDirect, Water Research 45 (2011), pp. 11-36, www.elsevier.com/locate/waters.
Grandstaff et al., Can Algae Solve a POTW's Nitrogen Removal Dilemma, Water Environment Federation 2011, pp. 7254-7267.
Chisti, Biodiesel from microalgae, Science Direct, 2007, Biotechnology Advances, pp. 294-306.
Beal et al., Comprehensive Evaluation of Algal Biofuel Production: Experimental and Target Results, Energies 2012, 5, pp. 1943-1981, www.mdpi.com/journal/energies.
Sturm et al., An energy evaluation of coupling nutrient removal from wastewater with algal biomass production, Applied Energy, 2011, pp. 1-8, www.elsevier.com/locate/apenergy.
Lundquist et al., Advances in Wastewater Treatment Pond Performance Using High Rate Ponds, Water Environment Federation, 2011, pp. 7294-7308, (WEFTEC 2011).
Hutton et al., Options for Energy From Algae at Wastewater Treatment Facilities, Water Environment Federation, 2011, pp. 7283-7293, (WEFTEC 2011).
Wang et al., Dynamics of Stoichiometric Bacteria-Algae Interactions in the Epilimnion, 2011, pp. 1-21.
Salerno et al., Biogas Production from Algae Biomass Harvested at Wastewater Treatment Ponds, an ASABE Conference Presentation, pp. 1-5, Paper No. Bio098023, Written for presentation at the 2009 Bioenergy Engineering Conference, Sponsored by ASABE, Seattle, WA, Nov. 12, 2009.
Aziz et al., Industrial wastewater treatment using an activated algae-reactor, Wat. Sci. Tech. vol. 28, No. 7, pp. 71-76, 1993, Pergamon.
Su et al., Municipal wastewater treatment and biomass accumulation with a wastewater-born and settleable algal-bacterial culture, Science Direct, Water Research 45 (2011), pp. 3351-3358, Elseiver.
Dalrymple et al., Wastewater use in algae production for generation of renewable resources: a review and preliminary results, Aquatic Biosystems, 2013, 9:2, pp. 1-11, http://www.aquaticbiosystems.org/content/9/1/2.
Ebling et al., Engineering analysis of the stoichiometry of photoautotrophic, autotrophic, and heterotrophic removal of ammonia-nitrogen in aquaculture systems, Aquaculture 257 (2006), pp. 346-358, www.sciencedirect.com.
Li et al., A Stoichiometrically Derived Algal Growth Model and Its Global Analysis, pp. 825-836, Mathematical Biosciences and Engineering, vol. 7., No. 4, Oct. 2010.
CATF White Paper, The Status of Algal Biofuel Development, CleanAir Task Force, pp. 1-17, Jul. 2013.
U.S. Environmental Protection Agency Combined Heat and Power Partnership, Oct. 2011, Opportunities for Combined Heat and Power at Wastewater Treatment Facilities: Market Analysis and Lessons from the Field, 57 pages, www.epa.gov/chp.
U.S. Department of Energy Biomass Program, National Algal Biofuels Technology Roadmap, 214 pages.
Global Bioengineering Partnership, Algae-Based Biofuels, A Review of Challenges and Opportunities for Developing Countries, May 2009, 60 pages.
Torres et al., Challenges for Cost-Effective Microalgae Anaerobic Digestion, Chapter 6, Intech, Biodegradation—Engineering and Technology, pp, 130-159, 2013. http://dx.dio.org/10.5772/55975.
U.S. Department of Energy, Energy Efficiency & Renewable Energy, Symbiosis Biofeedstock Conference: Expanding Commercialization of Mutualistic Microbes to Increase Biofeedstock Production, Dec. 2013, 39 pages.

(56) References Cited

OTHER PUBLICATIONS

Sheehan et al., National Renewable Energy Laboratory, NREL/TP-580-24190, A Look Back at the U.S. Department of Energy's Aquatic Species Program: Biodiesel from Algae, Close-Out Report, Jul. 1998, 328 pages.

Lundquist et al., A Realistic Technology and Engineering Assessment of Algae Biofuel Production, Energy Biosciences Institute, University of California, Berkeley, CA, Oct. 2010, 178 pages.

Sforza, Oil From Microalgae: Species Selection, Photobioreactor Design and Process Optimization, Università degli Studi di Padova, 173 pages.

Evans, Oxygen Dynamics in Algal Based Wastewater Treatment Systems, Submitted as a PhD thesis at Flinders University of South Australia, Mar. 2012, 280 pages.

Rothermel, Coupling the Wastewater Treatment Process with an Algal Photobioreactor for Nutrient Removal and Renewable Resource Production, Submitted to the Graduate Faculty of University of Pittsburgh, Swanson School of Engineering in partial fulfillment of the requirements for the degree of Master of Science in Civil Engineering, 2009, 107 pages.

Jalalizadeh, Development of an Integrated Process Model for Algae Growth in a Photobioreactor, University of South Florida, Scholar Commons, Graduate School Theses and Dissertations, 2012, 87 pages, http://scholarcommons.usf.edu/etd/4088.

Watson, A Thesis Presented to the Graduate School of Clemson University, in Partial Fulfillment of the Requirements for the Degree Master of Science Biosystems Engineering, May 2009, 222 pages.

Heimel, Anaerobic Co-digestion of Wastewater Treatment Pond Algae with Wastewater Sludge, A Thesis presented to the Faculty of California Polytechnic State University, San Luis Obispo, in Partial Fulfillment of the Requirements for the Degree Master of Science in Civil and Environmental Engineering, Dec. 2010, 45 pages.

Woertz, Lipid Productivity of Algae Grown on Dairy Wastewater as a Possible Feedstock for Biodiesel, A Master's Thesis Presented to the Faculty California Polytechnic University, San Luse Obispo, in Partial Fulfillment of the Requirements for the Degree Master of Science in Civil and Environmental Engineering, Dec. 2007, 87 pages.

Su, Settleable algal-bacterial culture for municipal wastewater treatment, Der Fakultät Nachhaltigkeit der Leuphana Universität Lüneburg zur Erlangung des Grades Doktorin der Naturwissenschaften, 1982 Dalian, China, 128 pages.

* cited by examiner

| | | | | | | | | BACTERIA | | |
|---|---|---|---|---|---|---|---|---|---|---|
| MOLAR | 1 CH₂O | + 0.142 | NH₄⁺ | + 0.29 | O₂ | + 0.142 HCO₃⁻ | --> | 0.142 C₅H₇O₂N | + 0.43 CO₂ | + 0.858 H₂O |
| MOLAR | 7.0 CH₂O | + 1.0 | NH₄⁺ | + 2.0 | O₂ | + 1.0 HCO₃⁻ | --> | 1.0 C₅H₇O₂N | + 3.0 CO₂ | + 6.0 H₂O |
| MASS | 211 CH₂O | + 18 | NH₄⁺ | + 65 | O₂ | + 61 HCO₃⁻ | --> | 113 C₅H₇O₂N | + 133 CO₂ | + 109 H₂O |
| | 85 AS MASS C | 14 AS MASS N | | 65 AS MASS O₂ | | | 60 AS MASS C | 36 AS MASS C | |
| | | | | | | | 14 AS MASS N | | | |

FIG. 12

| WASTEWATER CHARACTERISTICS | | | |
|---|---|---|---|
| | PARAMETER | VALUE | UNITS |
| | | 37793 | PE (POPULATION EQUIVALENTS) |
| | | 70 | GAL/PERSON |
| | FLOW | 10000 | m3/DAY |
| | FLOW | 2,645,503 | gpd |
| | | 2.65 | mgd |
| | BIODEGRADABLE COD | 300 | mg/L |
| | TKN - N | 30 | mg/L |
| | PO4 - P | 8 | mg/L |
| | ISS | 0 | mg/L |
| ELEMENTAL CONCENTRATION | | | |
| | PARAMETER | VALUE | UNITS |
| | C | 118 | mg/L |
| | N | 30 | mg/L |
| | P | 8 | mg/L |
| ELEMENT LOAD | | | |
| | PARAMETER | VALUE | UNITS |
| | C | 1176 | kg/DAY |
| | N | 300 | kg/DAY |
| | P | 80 | kg/DAY |

FIG. 13

| Influent flow, m3/d | | | | | | | | |
|---|---|---|---|---|---|---|---|---|
| 10,000 | | | | (conservative) | | | | |
| | times influent Q | Flow (gpm) | cfs | PSI | Head (feet) | Hyd Eff | BHP |
| Heterotrophic bioreactor recycle | 1.5 | 2756 | 6.14 | 0.7 | 1.6 | 65% | 1.73 |
| Autotrophic bioreactor recycle | 1.5 | 2756 | 6.14 | 1.4 | 3.3 | 65% | 3.50 |
| Effluent permeate pumping | 1 | 1837 | 4.09 | 20 | 46.2 | 65% | 32.97 |
| Operating costs | | | Daily Cost | Annual Cost | | | |
| 90% | 1.4 | $ 0.10 | $ 3.44 | $ 1,255 | | | |
| 90% | 2.9 | $ 0.10 | $ 6.97 | $ 2,542 | | | |
| 90% | 27.3 | $ 0.10 | $ 65.60 | $ 23,943 | | | |
| sum | 31.4 | | Annual power costs | 27,740 | | | |

FIG. 14

| Assumptions | |
|---|---|
| VSS destruction | 60% |
| | |
| Biogas yield, Primary Sludge (ft3 biogas/lb VSS digested) = | 15 |
| Biogas yield, Activated Sludge (ft3 biogas/lb VSS digested) = | 14 |
| Biogas yield, algae (ft3 biogas/lb VSS digested) = | 13 |
| | |
| biogas % methane | 65% |
| BTU/ft3 methane | 1000 |
| BTU/kWh | 3412 |
| kW/cfm methane | 17.6 |
| kW/cfm biogas | 11.4 |
| | |
| Microturbine efficiency | 0.26 |
| Microturbine power yield (kW/cfm) = | 2.97 |
| Biogas energy utilization = | 0.9 |
| | |
| electricity cost/kWh = | $0.10 |
| Per MGD | |
| VSS of primary sludge (lbs/mg/d) | 800 |
| VSS from Activated Sludge (lbs/mg/d) | 588 |
| VSS from Algae (lbs/mg/d) | 1084 |
| | |
| Total Biogas Production (ft3/d/mgd)) = | 20,598 |
| Biogas production rate (cfm/mgd) = | 14.3 |
| Power Generation Potential (kW(kW/mgd) = | 43 |
| kWh/mgd | 1020 |
| Annual power offset (kW-hr/mgd) = | 335,130 |
| Electricity revenue ($/mgd/yr)= | 33,513 |
| total VSS load to digestion (lbs/d/mgd) | 2,472 |
| For example | |
| Plant influent flow rate, m3/d | 10,000 |
| Total revenue from electricity | $88,659 |

FIG. 15

| (kWh/day, 10,000 m3/d plant) | | |
|---|---|---|
| | Wastewater treatment facility with a conventional activated sludge process | Wastewater treatment facility with a proposed dual - compartment bioreactor process |
| screens | 1 | 1 |
| aerated grit | 36 | 36 |
| primary clarifiers | 41 | 41 |
| aeration for carbon oxidation | 1410 | not needed |
| aeration for biological nitrification | 913 | not needed |
| return sludge pumping | 135 | not needed |
| secondary clarifiers | 41 | not needed |
| filter feed pumping | 218 | not needed |
| filtration | 86 | not needed |
| gravity thickening (for 1st. sludge) | 7 | 7 |
| dissolved air floatation (for 2nd. Sludge) | 536 | not needed |
| anaerobic digestion | 451 | 802 |
| belt filter press (for digested sludge) | 121 | 216 |
| chlorination | 7 | 7 |
| lighting and buildings | 212 | 212 |
| effluent permeate, and two recycle pumping systems for proposed dual-compartment bioreactor process | | 756 |
| TOTAL energy needs (-) | 4213 | 2082 |
| Energy Recovered from biogas combustion (+) | 1593 | 2703 |
| Net difference | -2620 | 621 |

FIG. 16

DUAL-COMPARTMENT BIOREACTOR FOR USE IN WASTEWATER TREATMENT AND ALGAL PRODUCTION

BACKGROUND

Wastewater has been treated with a variety of physical, chemical, and biological means over the last 100 plus years. Wastewater treatment typically includes a preliminary treatment process that screens debris and settles grit, a primary treatment process that physically removes larger particulates, a secondary treatment process that biologically removes smaller organic particulates and dissolved organics and recovers biological growth, optionally a tertiary treatment process that "polishes" secondary effluent by capturing remaining solids and removing remaining nutrients, and a disinfection process prior to discharge to receiving waters. The most common combination of secondary processes today are suspended growth biological treatment systems for oxidizing dissolved and particulate organics, which consist of bioreactors for biological growth and gravity settling clarifiers for recovering biomass. These systems are energy intensive because blowers are required to supply oxygen for oxidation of organic matter.

Suspended growth biological treatment (activated sludge) is conventionally performed in large bioreactors (tanks) that are supplied large amounts of oxygen and are usually open to the atmosphere. Of the 16,600 publically owned wastewater treatment facilities in the US, there are approximately 6,200 activated sludge facilities, ranging from very small (0.001 mgd) to very large (>800 mgd), treating nearly 80% of all flow. Activated sludge consists of microbial communities (primarily heterotrophic bacteria, but also protists, zooplankton, and annelids, and sometimes autotrophic nitrifying bacteria) and inert and biodegradable organic solids as fluffy solids collectively called "flocs" or "mixed liquor suspended solids" (MLSS). The microbial community, under high-rate operating conditions, is responsible for oxidation of both particulate and soluble carbonaceous matter in wastewater. The flocs are retained and separated from the clean effluent, typically via gravity settling. Excess growth of organisms and accumulation of solids are regularly removed from the system as excess activated sludge. Wastewater treatment in this manner is an energy intensive process, as up to 60% of the energy used at wastewater treatment plants is used to provide oxygen for biological treatment. Other secondary treatment processes include membrane bioreactors, sequencing batch reactors, integrated fixed-film activated sludge, trickling filters, oxidation ditches, treatment lagoons, etc.

Excess activated sludge biomass (waste activated sludge, or WAS) can be digested via anaerobic digestion along with settled solids collected from primary treatment processes (primary solids) to produce biogas that consists mostly of methane. The methane is burned for combined heat and power (CHP) systems at domestic wastewater treatment plants in the US. The theoretically smallest capacity wastewater treatment facility that can benefit from a CHP system is 1 mgd, which would make use of the smallest microturbine on the market today (30 kW). There are approximately 2,900 wastewater treatment facilities with anaerobic digestion processes in the US, with about 60% of plants over 10 mgd including anaerobic digestion. In the last few decades, the biogas produced from anaerobic digestion has begun to be used for heat for digester pre-heating, or for combined heat and power (CHP) systems that generate both heat and electricity at some of the larger domestic wastewater treatment plants in the US. Historically biogas was simply flared. As of 2004, there were nearly 250 digester gas utilization facilities that capitalized on this source of potential energy in some way (heat or CHP), with 76 actual CHP installations nationwide as of 2006 producing a total of 220 MW of power. The number of CHP systems is increasing as a result of today's escalating energy costs, and being implemented at smaller plants. Energy recovery from conventional treatment is typically between 0.15 and 0.2 kWh/m$^3$ of wastewater treated. A facility with anaerobic digestion and CHP can typically offset up to 50% of the energy requirements when compared to a facility without anaerobic digestion and CHP.

Algae (typically microalgae) production for biofuels and/or energy generation is currently in various stages of research and development. Some species of algae possess the ability to synthesize lipid storage compounds under certain growth conditions such as when stressed. High-lipid content algae contains from about 20 to about 50 weight percent lipids. High lipid content algae has a slower growth rate, and is more suitable for use in biofuel production processes than low lipid content algae. While most algae have autotrophic metabolisms (using inorganic carbon and light energy to produce more algae and oxygen), some species have heterotrophic metabolisms (using organic carbon for energy and growth, using oxygen to produce more algae and carbon dioxide), while others have mixotrophic metabolisms (exhibiting both autotrophic and heterotrophic metabolisms either simultaneously or depending on specific conditions).

Most commercial algal production has focused on photosynthetic, autotrophic species such as *Botryococcus braunii* and is expected to consist of high-rate algal ponds (HRAPs), photobioreactor (PBR) tubes or panels, or some combination of the two. HRAPs are shallow algal ponds or raceways open to the atmosphere, outdoors or in greenhouses, and include simple mechanical mixing. HRAPs typically consist of low concentrations of mixed cultures of algae with a lower lipid content in a much larger footprint, are susceptible to evaporative losses, contamination, competition by undesirable strains of algae, and predation by bacteria and zooplankton. HRAPs are simple and have a lower energy requirement for operation. PBRs are enclosed, transparent tubes, panels or bags tightly configured to maximize solar exposure either outdoors or in greenhouses. PBRs require mixing, flow-through pumping, and sparging of excess oxygen that can be toxic to algal growth. PBRs produce high concentrations of enrichment or pure cultures of algae with a greater lipid content in a much smaller footprint than HRAPs. PBRs also prevent evaporation and minimize contamination, predation and competition. PBRs are complicated and require more energy to operate than HRAPs. Both systems require supplemental carbon and/or nutrient addition to sustain sufficient to optimal algal production.

Recent work has focused on growing heterotrophic algae in fermenter-type bioreactors. The number of candidate strains is far fewer than for phototrophic growth, and include certain species within the genera *Chlorella, Tetraselmis*, and *Nitzschia*. Carbon sources can be glucose, glycerol, acetate, some or other carbon source, or waste carbon such as what is in wastewater. Nutrients such as nitrogen and phosphorus are required, and oxygen supply is critical. Without requiring light for growth, these systems are easier to scale and simpler to operate. Culture concentrations can be higher, as light transmission is not a factor, and growth rates can be greater. Much like autotrophic algal species, heterotrophic algal species can be induced to stimulate production of lipids which are valuable for the production of biofuels and other energy commodities. Heterotrophic algae produce carbon dioxide during respiration of organic carbon.

Algae production for biofuel energy has not yet reached large-scale commercialization due to technical and economic challenges. Biofuel from algae remains attractive because algae has dramatically more potential oil yield (between 1,000 and 4,000 gallons/acre/year) than the next highest-yielding biomass feedstock (oil palm, at 635 gallons/acre/year). Technical challenges for commercial algal production are primarily associated with the performance of dewatering technologies. Operating costs for algal production, including supplementation with carbon and nutrients, can also be high. Waste carbon sources (e.g., carbon dioxide from gaseous emissions from power plants for autotrophs; organics in industrial and domestic wastewaters for heterotrophs), have been targeted to reduce operating costs and sequester carbon. Technical challenges for commercial biofuel production from algae are primarily associated with processing/drying dewatered algae and extracting lipids. It has been recognized that direct fermentation/digestion of dewatered algae and electricity generation from the resulting biogas is currently the most cost effective method of recovering energy from algae.

It would be desirable to develop new systems and methods for wastewater treatment that reduce or eliminate the need for oxygen supplementation for removal of organic matter.

It would be desirable to develop new systems or methods for wastewater treatment that reduces nutrients such as nitrogen and phosphorus from effluents discharged to receiving waters.

It would be desirable to develop new systems or methods for wastewater treatment that reduces metals such as chromium, copper, and zinc from effluents discharged to receiving waters.

It would be desirable to develop new systems and methods for wastewater treatment that reduce energy use, produce energy to offset energy needs for treatment, or produce more energy than is needed for treatment.

It would be desirable to develop new systems and methods for wastewater treatment that reduce or eliminate supplemental oxygen need for nitrification of ammonia in wastewater.

It would be desirable to develop new systems and methods for wastewater treatment that reduce or eliminate the release of greenhouse gases through heterotrophic respiration.

It would be desirable to develop new systems and methods for wastewater treatment that increase biogas production per unit volume of wastewater treated.

It would be desirable to develop new algal production systems and methods that reduce or eliminate the need for carbon supplementation for autotrophic algal production.

It would be desirable to develop new algal production systems and methods that reduce or eliminate the need for oxygen supplementation for heterotrophic algal production.

It would be desirable to develop new algal production systems and methods that reduce or eliminate the potential for oxygen toxicity for autotrophic algae.

It would be desirable to develop new algal production systems and methods that reduce or eliminate the need for nutrient supplementation for heterotrophic and autotrophic algal production.

BRIEF DESCRIPTION

A dual-compartment bioreactor system comprises a bioreactor primarily intended for photosynthetic, autotrophic respiration, a second bioreactor primarily intended for heterotrophic respiration, and a membrane subsystem in operational contact with both bioreactors. The autotrophic bioreactor includes a transparent outer wall. Transport of solutes and gasses across the membrane allows for beneficial use by one population of the metabolic products of the other while separating the populations to ensure optimal growth and function of each.

Methods for metabolizing inputs (e.g., treating wastewater and producing algae) with the dual bioreactor system are also disclosed.

BRIEF DESCRIPTION OF THE DRAWINGS

FIGS. 11 through 16 show calculations made as part of a proof of concept exercise.

DETAILED DESCRIPTION

Figure 1:
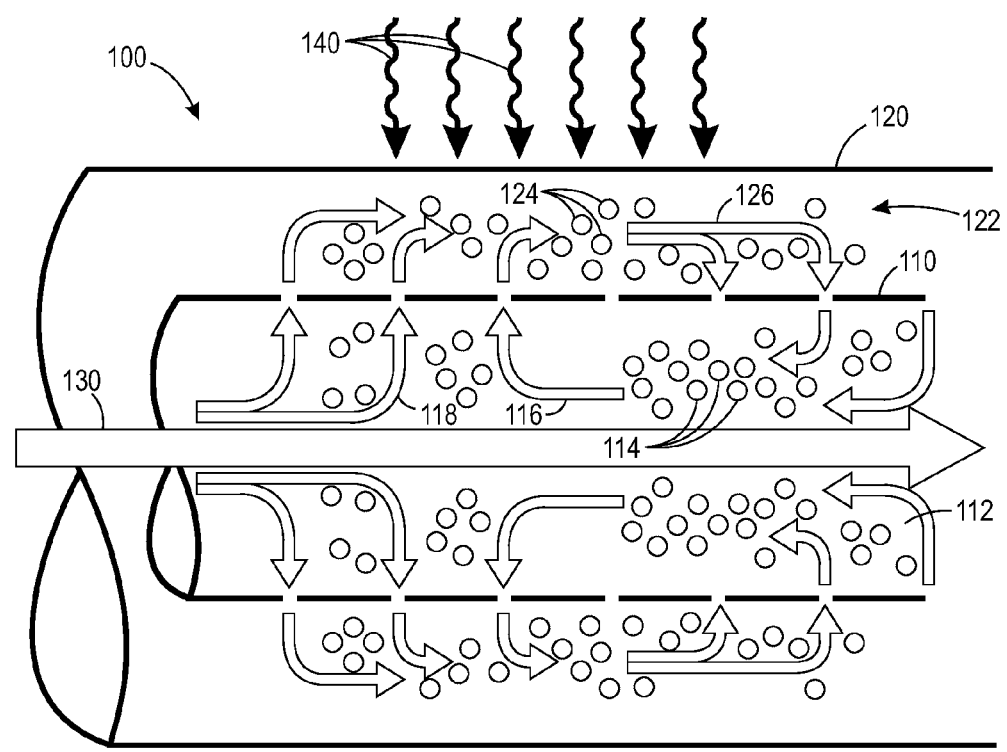
FIG. 1 is a cross-sectional view of an exemplary embodiment of a tube within a tube dual compartment bioreactor configuration of the present disclosure, applicable for both wastewater treatment and algal growth applications.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, along with any impurities that might result therefrom, and excludes other components/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 to 10" is inclusive of the endpoints, 2 and 10, and all the intermediate values).

A value modified by a term or terms, such as "about" and "substantially," may not be limited to the precise value specified. The approximating language may correspond to the precision of an instrument for measuring the value. The modifier "about" should also be considered as disclosing the range defined by the absolute values of the two endpoints. For example, the expression "from about 2 to about 4" also discloses the range "from 2 to 4."

As used herein, the term "operational contact" does not require or exclude direct contact. One or more intermediate elements (e.g., tubing, storage tanks, etc.) are optionally between structures that are in operational contact. When structures are in operational contact, transport may occur there between.

As used herein, the term "membrane subsystem" refers to a subsystem that comprises one or more membranes. When multiple membranes are included, the membranes may be of the same type or different types. The membranes may be in operational contact including direct contact.

Unlike existing wastewater treatment technologies, the systems and methods of the present disclosure (1) provide a free source of oxygen from photosynthesis for heterotrophic carbon oxidation (waste degradation) and autotrophic nitrification from photosynthesis; and (2) provide a free source of carbon dioxide for autotrophic algal growth. This symbiosis reduces overall wastewater treatment facility energy requirements (e.g., by 50%), and increases (e.g., almost doubles) the biogas potential (and hence heat and energy potential via cogeneration) per unit volume wastewater through excess algae production (added to existing excess activated sludge and primary solids digester feedstocks).

Unlike existing algal production technologies, the systems and methods of the present disclosure (1) provide a free source of oxygen from photosynthesis for growth of heterotrophic algae; and (2) provide a free source of carbon dioxide from heterotrophic carbon oxidation for autotrophic algal growth. This symbiosis reduces energy requirements and increases algal production.

Unlike existing closed system (photobioreactor, PBR) algal production technologies, the systems and methods of the present disclosure reduce or prevent toxic accumulation of oxygen due to the oxygen demand exerted by heterotrophic organisms for carbon oxidation.

The system 100 of FIG. 1, shown here for wastewater treatment applications and for algal production applications, includes a membrane 110 and an outer transparent wall 120. The membrane 110 defines an inner compartment which is intended primarily for heterotrophic respiration (either by activated sludge or heterotrophic algae), and is the heterotrophic bioreactor 112. The outer transparent wall 120 and membrane 110 define an outer compartment which is primarily intended for photosynthetic, autotrophic photosynthesis (primarily by autotrophic algae), and is the autotrophic bioreactor 122. The inputs 130 (either a wastewater having undergone primary treatment (primary effluent) containing organic carbon wastes and waste nutrients, a produced feedstock containing manufactured organic carbon substrates and manufactured nutrients, or some combination thereof) is fed to the inner compartment/heterotrophic bioreactor 112 and transferred to a process to separate and recover heterotrophs (e.g., using a membrane similar to what is used in an immersed membrane bioreactor (MBR)). Organisms 114 in the heterotrophic bioreactor 112 produce carbon dioxide 116. The membrane 110, process operation, and/or reactor geometry is configured to permit carbon dioxide 116 and nutrients 118 from the heterotrophic bioreactor 112 to pass through the membrane to the phototrophic bioreactor 122. Light (e.g., sunlight) 140 passes through the transparent outer wall 120 to the autotrophic algae 124. The autotrophic algae 124 produce oxygen 126. The membrane 110, process operation, or reactor geometry are configured to permit the oxygen 126 to pass from the autotrophic bioreactor 122 to the heterotrophic bioreactor 112. Nutrients 118 from the input 130 also pass through the membrane 110 to the autotrophic bioreactor 122.

Therefore, the heterotrophic and autotrophic populations are contained in distinct compartments, with the two populations of organisms separated from each other by one or more membranes (e.g., a sheet membrane or a tube membrane).

Although the depicted embodiment includes a tube within a tube structure, the compartments 112, 122 alternatively may be stacked such that the autotrophic bioreactor 122 faces a light source (e.g., the sun) and is located between the heterotrophic bioreactor 112 and the light source.

The length of the heterotrophic bioreactor 112 and the autotrophic bioreactor 122 may be the same or different. In some embodiments, the length of the heterotrophic bioreactor 112 is at least about 2 feet, including from about 1 foot to about 100 feet and from about 10 feet to about 50 feet. In some embodiments, the length of the autotrophic bioreactor is at least about 2 feet, including from about 1 foot to about 100 feet and from about 10 feet to about 50 feet.

In tube within a tube embodiments, the heterotrophic bioreactor may have an inner diameter of from about 1 inch to about 5 feet, including from about 6 inches to about 3 feet, and from about 1 foot to about 2 feet.

The autotrophic bioreactor 122 may have an inner diameter of from about 2 inches to about 6 feet, including from about 6 inches to about 3 feet and from about 1 foot to about 2 feet.

The transparent outer wall may have a thickness of from about 0.1 inch to about 1 inch, including from about 0.25 inch to about 0.75 inch, and from about 0.3 inch to about 0.6 inch. The transparent outer wall will be fully or partially transparent to visible light (~400-800 nm) wavelengths, as those are the wavelengths used by algae during photosynthesis.

The membrane 110 may be a composite membrane including a main membrane layer anchored or bonded to a substrate layer or a main membrane layer without a substrate layer. The main membrane layer may contain a fluorine-containing polymer (e.g., polyvinylidene fluoride or PVDF). The substrate layer may contain a polyolefin (e.g., polyethylene) or a fluorine-containing polymer. The fluorine-containing polymer of the main membrane layer and the substrate layer may be the same or different. The membrane may be hydrophobic, hydrophilic, or some combination thereof. The membrane may be parallel, ribbed, curved, pleated, bulbous, helical, or tapered in relation to the outer wall.

The membrane 110 may include pores having a diameter of about 0.0001 μm to 10 μm, including from about 0.1 μm to about 1 μm and from about 0.01 μm to 0.1 μm.

The transparent outer wall 120 may generally be made of any transparent material with sufficient mechanical properties. Non-limiting examples include polycarbonates, acrylic polymers (e.g., poly(methyl methacrylate)), acrylonitrile-butadiene-styrene terpolymers, and polystyrenes (e.g., high impact polystyrene) or glass. In some embodiments, one or more of these components may be blended and/or copolymerized together. The outer wall may be ribbed, curved, pleated, bulbous, helical, or tapered in relation to the membrane.

Although wastewater treatment and algae production are specifically disclosed, it should be understood that methods of metabolizing other inputs using the systems and apparatuses of the present disclosure are also contemplated. In the wastewater treatment methods, the inputs may include waste organic substrates and waste nutrients and the wastewater may be a domestic wastewater, an industrial wastewater, a food processing wastewater, or an agricultural (e.g., dairy, piggery, and feedlot) wastewater. In the algae production methods, the inputs may include manufactured organic substrates and manufactured nutrients. It should also be noted that the systems and methods of the present disclosure may be used simultaneously for both wastewater treatment and algae production.

The systems and methods of the present disclosure may be used in existing wastewater treatment facilities (i.e., retrofitting) or in new construction (greenfield), may be used as the exclusive secondary treatment process, and/or may be used to supplement other secondary treatment processes.

The systems and methods of the present disclosure may be installed or mounted on or above existing infrastructure such as on rooftops, above parking lots, in highway verges, or above existing wastewater treatment infrastructure (e.g., aeration tanks or clarifiers).

The systems and methods of the present disclosure may consist primarily of algae in both compartments of the dual compartment bioreactor system for the sole purpose of generating feedstocks for biofuel. The heterotrophic bioreactor may contain heterotrophic algae that oxidize organic carbon using oxygen and generate more heterotrophic algae and carbon dioxide, and the outer compartment may contain autotrophic algae, which use the carbon dioxide and light to produce more autotrophic algae and oxygen. Transport of solutes and gases across the membrane allows for beneficial use by one population of the metabolic products of the other while separating the populations to ensure optimal growth and function of each.

The systems and methods of the present disclosure allow for the optimal symbiosis of two different types of mixed or pure cultures of organisms for wastewater treatment, algal production, or both.

The systems and methods of the present disclosure may be used to treat domestic wastewaters, municipal wastewaters, industrial wastewater, or agricultural wastewaters.

The systems and methods of the present disclosure may rely exclusively on natural light (solar radiation), partly on natural light and partly on artificial light, or exclusively on artificial light.

The systems and methods of the present disclosure may rely wholly or in part on manufactured substrates, electron donors and acceptors, and/or nutrients when the primary objective is algal production.

The systems and methods of the present disclosure may rely wholly or in part on waste substrates, electron donors and acceptors, and/or nutrients when the objective is either wastewater treatment or algal production.

The systems and methods of the present disclosure may include means to supply supplemental inorganic carbon (e.g., carbon dioxide) if inorganic carbon generation (via heterotrophic respiration) or transport across the membrane is insufficient for adequate autotrophic growth. Such means may include dissolved inorganic carbon monitoring in both the autotrophic bioreactor and the heterotrophic bioreactor and an automated inorganic carbon delivery mechanism.

The systems and methods of the present disclosure may include means to supply supplemental oxygen if oxygen generation (via autotrophic photosynthesis) or oxygen transport across the membrane is insufficient for adequate carbon oxidation and heterotrophic growth. Such means may include dissolved oxygen monitoring in both the autotrophic bioreactor and the heterotrophic bioreactor and an automated oxygen delivery mechanism.

The systems and methods of the present disclosure may include means to control transport of gasses or solutes across the membrane. Such means could include controlling the recycle flow rates of the heterotrophic and autotrophic bioreactors, with the intent of developing pressure differences (pressure drops) across the membrane. In some embodiments, valves are used to control and modify pressure differences. Such pressure differences would then drive liquid flow (the carrier for gasses and solutes) across the membrane from regions of higher pressure to regions of lower pressure. Flow rate would be driven by pressure drop, not by the actual pressure. Depending on the pressure regime, this may facilitate transport from the heterotrophic bioreactor to the autotrophic bioreactor, or from the autotrophic bioreactor to the heterotrophic bioreactor. Sufficiently high pressure drops would ensure sufficient transport as needed for various biological reactions. Recycle flows could be counter current or concurrent to influence these pressure differences. Pressure differences could also be developed by connecting modules in series or parallel, and between modules could be the same or different for heterotrophic and autotrophic bioreactor components of the same module (e.g., heterotrophic bioreactor compartments could be connected in series, while autotrophic bioreactor compartments could be connected in parallel). Dissolved oxygen or carbon dioxide monitoring in both the algal bioreactor and the heterotrophic bioreactor, in addition to the rate of oxygen supplementation or inorganic carbon supplementation, could be used as a means to verify that dissolved oxygen and/or dissolved inorganic carbon is beneficially being transported across the membrane and reducing the amount of oxygen or inorganic carbon that would otherwise be needed for carbon oxidation by heterotrophs or growth of autotrophs, respectively. Recycle flows could be increased until the rate of inorganic carbon or oxygen supplementation stops changing (or stops all together), signifying the maximal rate of transport of products across the membrane.

The systems and methods of the present disclosure may include means to control transport of gasses and/or solutes across the membrane. Such means may include a novel membrane that incorporates hydrophobic and hydrophilic regions, or a system of modules wherein some modules contain hydrophilic membranes and some modules contain hydrophobic membranes. The hydrophilic membranes allow for the transport of fluids, solutes and gases across the membrane, while the hydrophobic membranes only allows for the transport of gasses across the membrane. Driving transport for fluids, solutes or gases would require establishing a pressure drop which could be controlled by altering recycle rates for hydrophilic membrane embodiments.

The systems and methods of the present disclosure may include means to control transport of gasses and/or solutes across the membrane. Such means may include a novel reactor geometry that forces flow back and forth across the membrane by creating local pressure drops that result from the reactor geometry. An embodiment would be a plate reactor configuration with parallel but undulating top and bottom. The membrane separating the autotrophic bioreactor from the heterotrophic bioreactor would be flat. Therefore the cross sections of each bioreactor compartment would increase and decrease, complimented by a corresponding decrease and increase of the other bioreactor compartment. In this way flow is forced back and forth across the membrane.

The systems and methods of the present disclosure may rely wholly or in part on osmosis for the transport of gasses and/or solutes across the membrane.

The system and methods of the present disclosure may include means to control pH and alkalinity in the autotrophic bioreactor and the heterotrophic bioreactor. Such means would include pH and alkalinity monitoring in both the autotrophic bioreactor and the heterotrophic bioreactor and an automated chemical dosing mechanism.

The systems and methods of the present disclosure may include means to control light exposure to the autotrophic bioreactor to moderate photosynthesis and the production of oxygen. Such means would include light intensity monitoring and the ability to control light exposure such as with blinds, drapes, covers, opaque sleeves, or other light-blocking devices. Such means of control may also include the ability to supply artificial light as needed.

Figure 2:
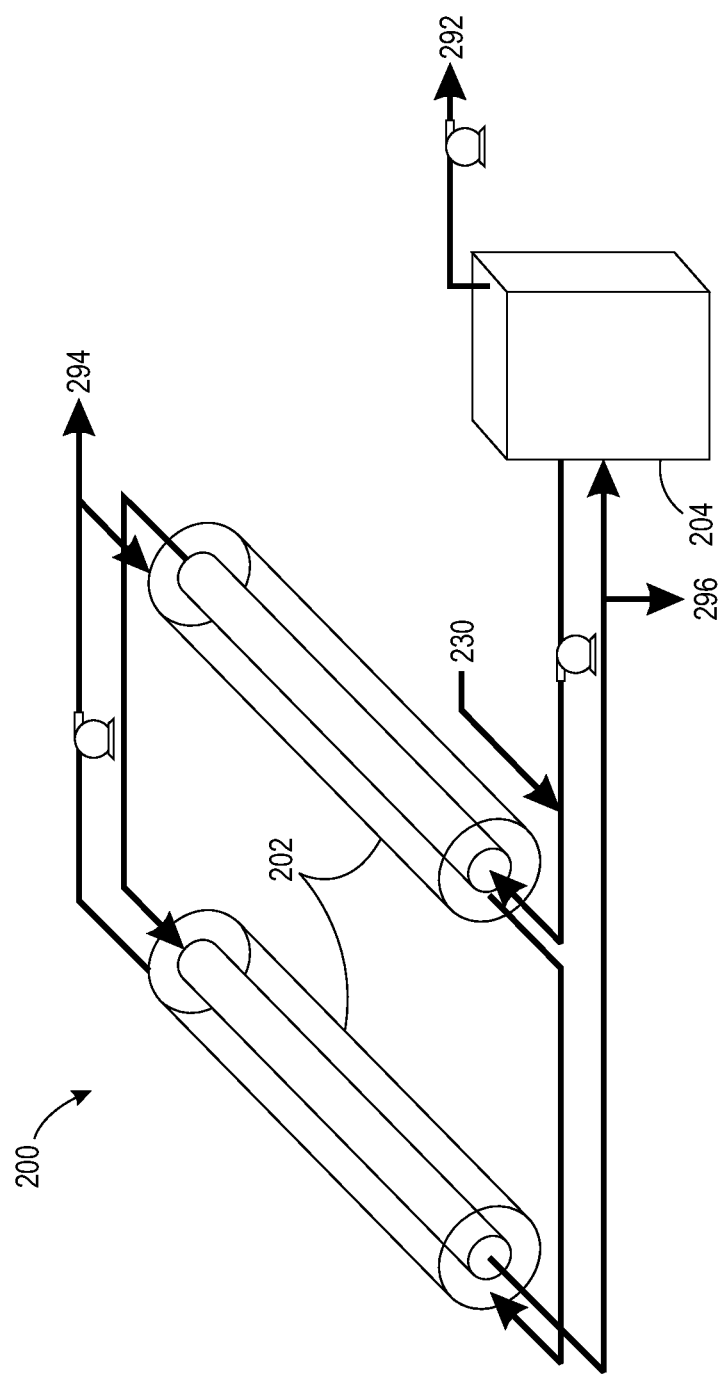
FIG. 2 is a perspective view of an exemplary embodiment of a wastewater treatment system utilizing two dual compartment bioreactors.

The system 200 of FIG. 2, shown here for wastewater treatment applications, includes two dual-compartment bioreactor modules 202 along with a final membrane 204, similar in feature and function to existing membrane bioreactor (MBR) technologies, for producing clean effluent 292 from wastewater 230 by separating the activated sludge from the treated effluent. The final membrane proposed herein, while similar to what is used in existing MBR technologies, may not be an entire MBR process with corresponding design elements (solids residence times, volumes for treatment, etc.) as if it were to provide the same level of treatment of an MBR. The membrane here may simply be the membrane in an appropriate enclosure. The system 200 also produces excess organisms from the autotrophic bioreactor 294 and excess organisms from the heterotrophic bioreactor 296. If the final membrane is of a flat panel or immersed/submerged type, the final membrane may have a flat-panel configuration or a hollow fiber configuration, with each of these configurations including immersed/submerged cassettes of cartridges. In some embodiments, the final membrane is similar to what is used in a Siemens Zeeweed MBR or Kubota flat-panel submerged membrane unit (SMU). If of a sidestream type, the final membrane may have a tubular configuration. In some embodiments, the final membrane is a Porex TMF cross-flow tubular membrane module.

Figure 3:
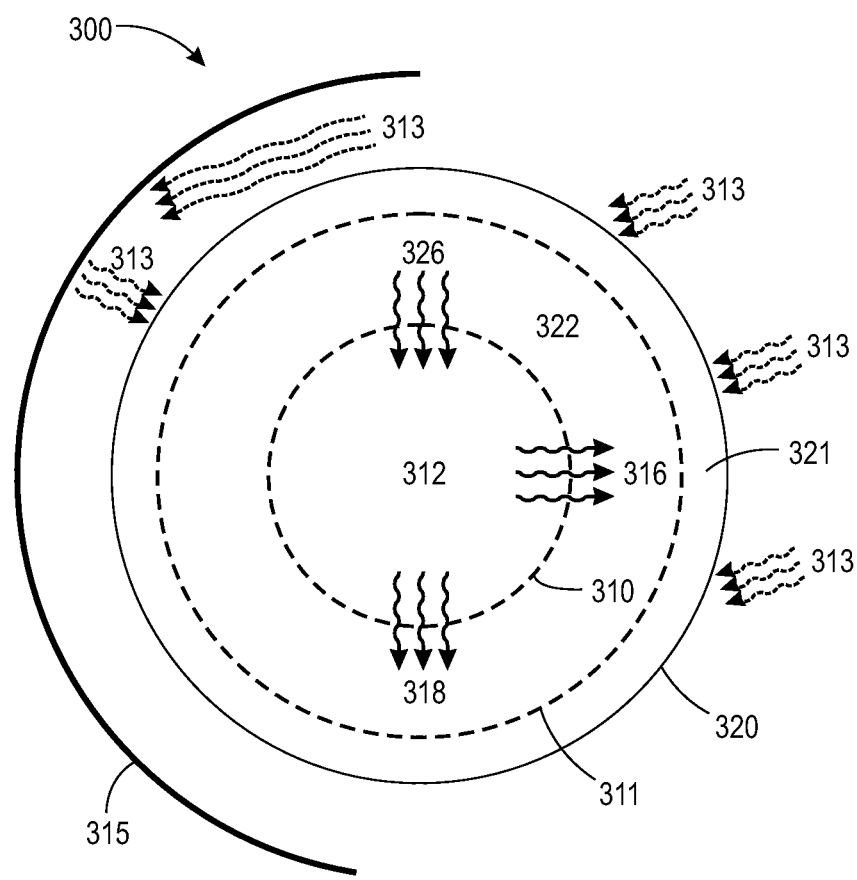
FIG. 3 is a cross-sectional view of another exemplary embodiment of a tube within a tube dual compartment bioreactor configuration of a wastewater treatment system of the present disclosure.

The system 300 of FIG. 3, shown here for wastewater treatment applications, includes an inner membrane 310, an outer membrane, 311, and a transparent outer wall 320. The outer membrane 311 is sufficiently transparent to visible light to allow photosynthesis to occur. Optionally, the system further includes one or more light sources 313 and/or one or more light concentrators 315. In some embodiments, the light concentrator 315 is a parabolic concentrator. The inner membrane 310 defines an inner compartment/heterotrophic bioreactor 312. The inner membrane 310 and outer membrane 311 define a second compartment/autotrophic bioreactor 322. The outer membrane 311 is the final membrane, forgoing the need for an MBR as final membrane 204 shown in FIG. 2. The transparent outer wall 320 and outer membrane 311 define a passageway 321 for clean water. The membrane 310, process operation, and/or reactor geometry can be configured to allow carbon dioxide 316 and nutrients 318 to pass from the heterotrophic bioreactor 312 to the autotrophic bioreactor 322 and to allow oxygen 326 to pass from the autotrophic bioreactor 322 to the heterotrophic bioreactor 312.

Figure 4A:
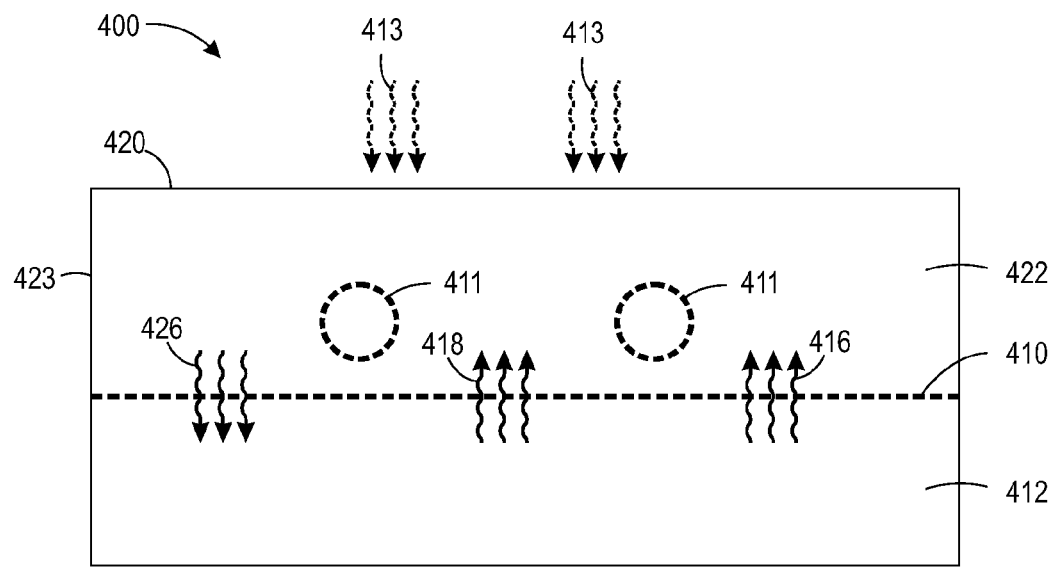
FIGS. 4A and 4B are cross-sectional views of two exemplary embodiments of dual compartment bioreactors of a wastewater treatment system of the present disclosure.
Figure 4B:
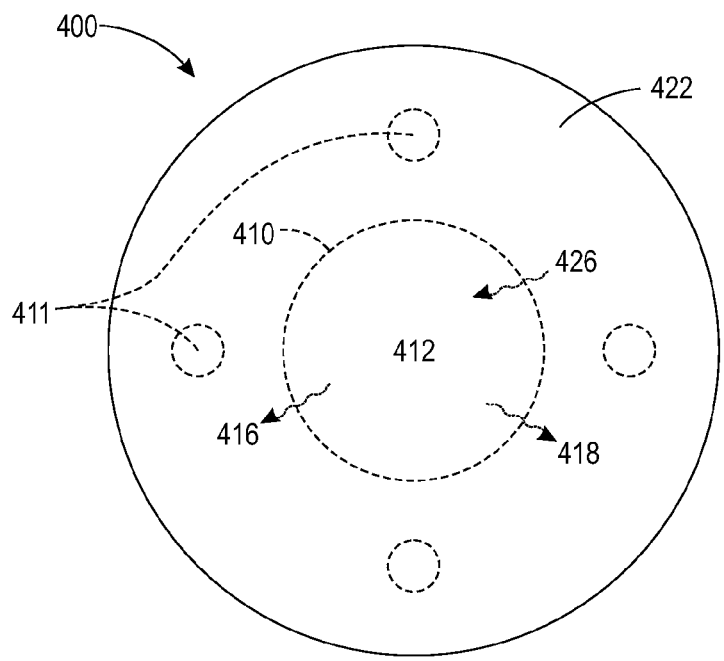

In another embodiment, shown here for wastewater treatment applications, a panel-type reactor module 400 of FIG. 4A includes a membrane 410 separating a first compartment/heterotrophic bioreactor 412 from a second compartment/autotrophic bioreactor 422. The module 400 further includes a transparent outer wall 420. Optionally, clean, treated water is removed via membrane tubes 411 located inside the autotrophic bioreactor, forgoing the need for a final membrane such as an MBR 204 shown in FIG. 2. An outer case 423 may be made of any material with sufficient properties to prevent leakage and need not be transparent. In some embodiments, the outer case 423 is made of stainless steel. The membrane 410, process operation, and/or reactor geometry can be configured to permit carbon dioxide 416 and nutrients 418 to pass from the heterotrophic bioreactor 412 to the autotrophic bioreactor 422 and to permit oxygen 426 to pass from the autotrophic bioreactor 422 to the heterotrophic bioreactor 412, e.g. by modulating pressure drops as described above for a previous embodiments. The module 400 of FIG. 4B is similar to the module of FIG. 4A but has a substantially cylindrical configuration instead of a panel-type configuration.

Figure 5:
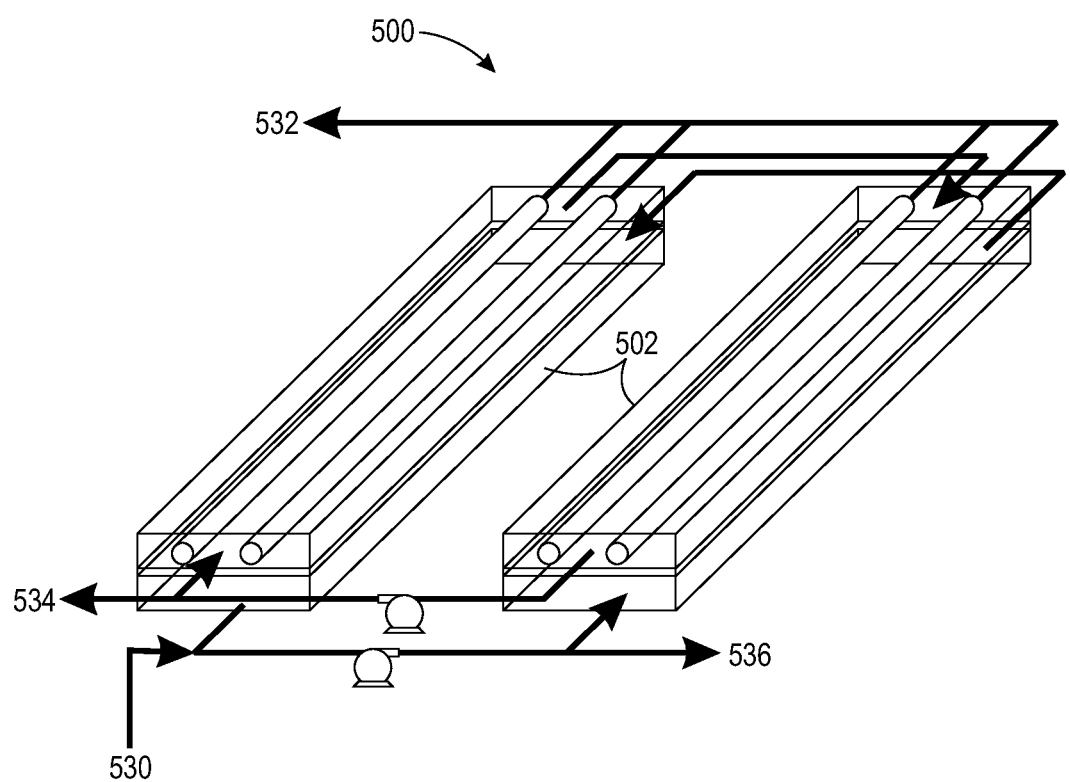
FIG. 5 is a perspective view of an exemplary embodiment of a wastewater treatment system utilizing two panel-type dual compartment bioreactors.

The system 500 of FIG. 5 includes two panel-type reactor modules 502 similar to the configuration shown in FIG. 4A. Wastewater 530 is fed to the system 500 and clean water 532 is recovered. Excess heterotrophic growth 536 and excess autotrophic growth 534 may also be recovered.

In some embodiments when the application is wastewater treatment, the ratio of Carbon:Nitrogen:Phosphorus (C:N:P) in the wastewater is not optimal for maximum algae production and additional inorganic carbon is added (e.g., via injection of flue gases rich in carbon dioxide by known processes such as cogeneration of electricity and heat by biogas combustion) to increase autotrophic growth if the objective is to either maximize algal production or to maximize nutrient removal via assimilation for cell growth.

In other embodiments when the application is wastewater treatment, the systems and methods of the present disclosure do not require additional inorganic carbon if the objective is solely to remove organics from wastewater and accomplish nitrification and some nutrient removal.

In some wastewater treatment embodiments when the heterotrophic population is activated sludge, organic carbon can be added to the heterotrophic bioreactor to improve reduction of nitrate to nitrogen gas (denitrification) when oxygen is depleted.

In some wastewater treatment embodiments, metal salts (trivalent metal ions such as ferric chloride, aluminum sulfate) can be added to either the autotrophic or heterotrophic bioreactor to improve orthophosphate removal if phosphorus uptake via assimilation for cell growth is insufficient to meet effluent nutrient criteria.

In some wastewater treatment embodiments, the systems and methods allow the elimination of outside inputs, including energy. The combination of excess autotrophic and heterotrophic growth may be used to increase biogas yields in onsite anaerobic digesters to achieve energy positivity.

In algae production embodiments, the autotrophic and heterotrophic populations can be either a pure culture of a single strain, an enrichment culture of mostly the same strain, or a mixed culture of different strains of organisms.

In some embodiments, the algae removes heavy metals and other contaminants from the wastewater via biosorption. Accumulated heavy metals are removed from the system when excess algal growth is removed.

In some embodiments, the algal photosynthesis bioreactor contents may be recirculated for mixing and to enhance diffusion. Diffusion of oxygen from the algal photosynthesis bioreactor to the activated sludge bioreactor may rely on osmotic pressure.

Separating the autotrophic and heterotrophic populations creates flexibility in process control that allows process optimization whether for wastewater treatment, excess autotroph production, or excess heterotrophic production. Such separation allows for optimal control of environmental conditions (e.g., pH, temperature, pressure, flux rates, salinity, alkalinity, solids residence times, concentrations of different populations, hydraulic residence times, etc.).

Separating autotrophic and heterotrophic populations protects autotrophic organisms from predation by heterotrophic organisms.

Figure 6:
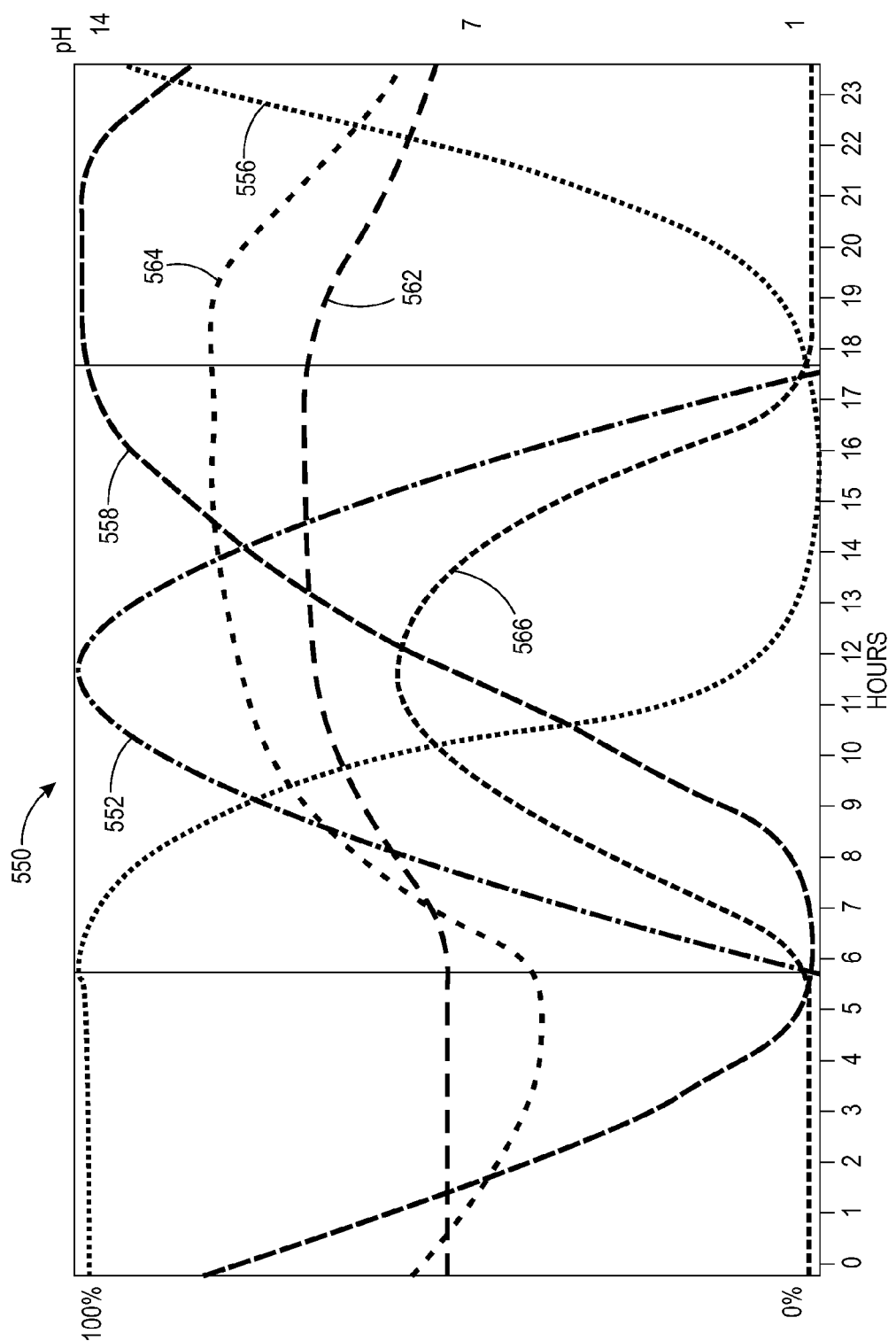
FIG. 6 is a graph illustrating system dynamics.

The relative volumetric relationships between the bioreactors, the recirculation rates within each bioreactor, and the ideal flow rates through the system will depend on the kinetics and stoichiometric relationships of the populations used (types of heterotrophs and types of autotrophs), whether heterotrophic carbon sources are wastes or feedstocks, and the intended application (wastewater treatment, algal production, or both). The complex and dynamic relationships between carbon sources, electron donors, electron acceptors, pH, and alkalinity can be explored with a process model. An estimated relationship between these variables for a wastewater treatment application using activated sludge in the heterotrophic bioreactor and autotrophic algae in the autotrophic bioreactor over the course of a day is illustrated by graph 550 of FIG. 6 as shown by light intensity 552, ammonium concentration 556, nitrate concentration 558, pH 562, bacterial growth rate 564, and algal growth rate 566. Commercially available simulators (e.g., BioWin, GPS-X) exist for wastewater process design and evaluation. The models are codifications of partial differential equations based on Monod-type kinetics and relationships. Typical solids residence times for the activated sludge bioreactor may be between 2 and 20 days, with solids concentrations between 2,000 and 20,000 mg/L. Typical solids residence times for algal bioreactors may be between 2 and 20 days, with solids concentrations between 1,000 and 8,000 mg/L. The recirculation rates for each system may be between 0.2× and 5× the influent flow rate. The relative volume of the algal bioreactor may be between 0.5× and 5× the activated sludge bioreactor volume.

Generally, reducing the pore size in a membrane leads to increased head loss, greater pumping requirements, and lower flux rates. The membranes used in the systems and methods of the present disclosure may be similar to flat panel membranes (e.g., Kubota's submerged membrane unit or SMU) or similar to tubular membranes (e.g., Porex TMF cross-flow tubular membrane modules). Kubota's SMU microfiltration panel cartridges have a nominal porosity of 0.4 μm, sufficient for retention of both activated sludge and algae. The cartridges are designed to operate at a flux rate of 15 gpd/sf and at typical trans-membrane pressures of 0.7 to 2 psig when operated at a MLSS of 10,000 mg/L. While the trans-membrane pressure is the relative difference in pressure across a membrane, the operating pressure for the membrane system is what the pump sees and is important in calculating operating costs. Typical microfiltration MBRs used in wastewater treatment have operating pressures of 20 to 40 psi. The membranes in the systems and methods of the present disclosure (e.g., a tubular membrane that defines the activated sludge bioreactor) may have trans-membrane and operating pressures between 1 and 10 psi. Net flow through this membrane may be less than 5% of the influent flow. Estimated flow rates across this membrane may be about 15% of the flow rate through a typical immersed MBR membrane.

The membranes may be reverse osmosis membranes, nanofiltration membranes, ultrafiltration membranes, and/or microfiltration membranes. Properties of these types of membranes are provided in the table below from Water Environment Federation Manual of Practice #8.

| Parameter | Reverse Osmosis | Nanofiltration | Ultrafiltration | Microfiltration |
| --- | --- | --- | --- | --- |
| Molecular Weight cutoff (MWCO), Da | <100 | 100-1,000 | 1,000-100,000 | >100,000 |
| Particle size average range, μm | <0.0001 | 0.0001-0.001 | 0.001-0.01 | 0.1-0.5 |
| Level of treatment/removal | TDS | Hardness, TDS partially | Viruses | Suspended solids, bacteria, pathogens |

-continued

| Parameter | Reverse Osmosis | Nanofiltration | Ultrafiltration | Microfiltration |
|---|---|---|---|---|
| Rejection/ removal % | Up to 99.7% TDS | Up to 50% TDS, >80% hardness | Up to 99.9999% particles, up to 99.99% pathogens and viruses | Up to 99.9999% particles, up to 99.99% pathogens, and up to 99% viruses |
| Membrane shape/type | Spiral wound | Spiral wound | Hollow fiber, flat sheet | Hollow fiber, flat sheet |
| Membrane materials | TFC, polysulfone (PSF), cellulose acetate (CA) | TFC, CA | PVDF, PSF, polytetrafluoro ethylene (PTFE), polyether sulfone (PES) | PVDF, PSF, PTFE, PES, polypropylene, nylon |

The systems and methods of the present disclosure may use a cleaning device or method for membrane cleaning. Current membrane cleaning methods in the wastewater industry include intermittent back pulsing, chemical clean-in-place processes, and intermittent air scouring. In some embodiments the cleaning method may include intermittent back-pulsing or chemically cleaning in place. The most common membrane cleaning technology involves intermittent air scouring (membrane aeration), which requires almost as much energy as providing air and oxygen for the biological process (bioprocess aeration) for membrane bioreactor applications. In some embodiments the cleaning method may include intermittent scouring with air or waste flue gas, which may also provide supplemental inorganic carbon for algal photosynthesis.

In some embodiments, the cleaning device includes magnetically activated elements (e.g., electromagnetically activated brushes) that are permanently located in the system (e.g., on one or both sides of the membrane). An externally mounted magnet may engage the brushes and may travel the length of the activated sludge bioreactor, pulling and/or spinning the brush(es) to clean the inside and/or outside membrane surface on an intermittent or continuous basis. In some embodiments, an additional brush may be configured to clean an internal surface of the transparent outer wall in order to reduce biofouling.

Figure 7A:
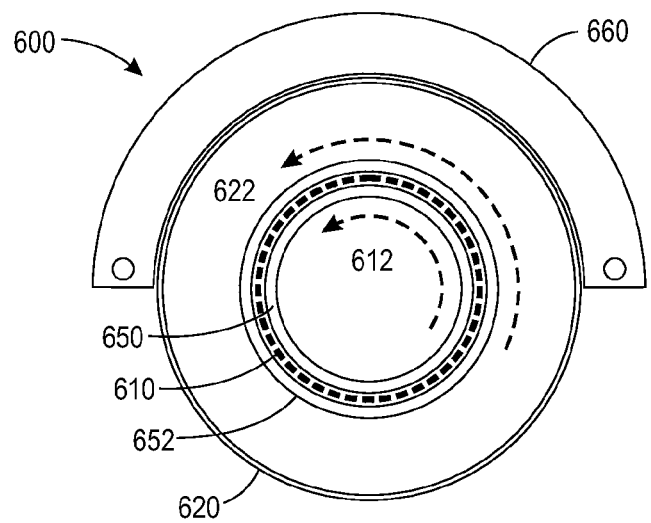
FIG. 7A is a cross-sectional view of an exemplary embodiment of a wastewater treatment system of the present disclosure including a mechanism for membrane cleaning.
Figure 7B:
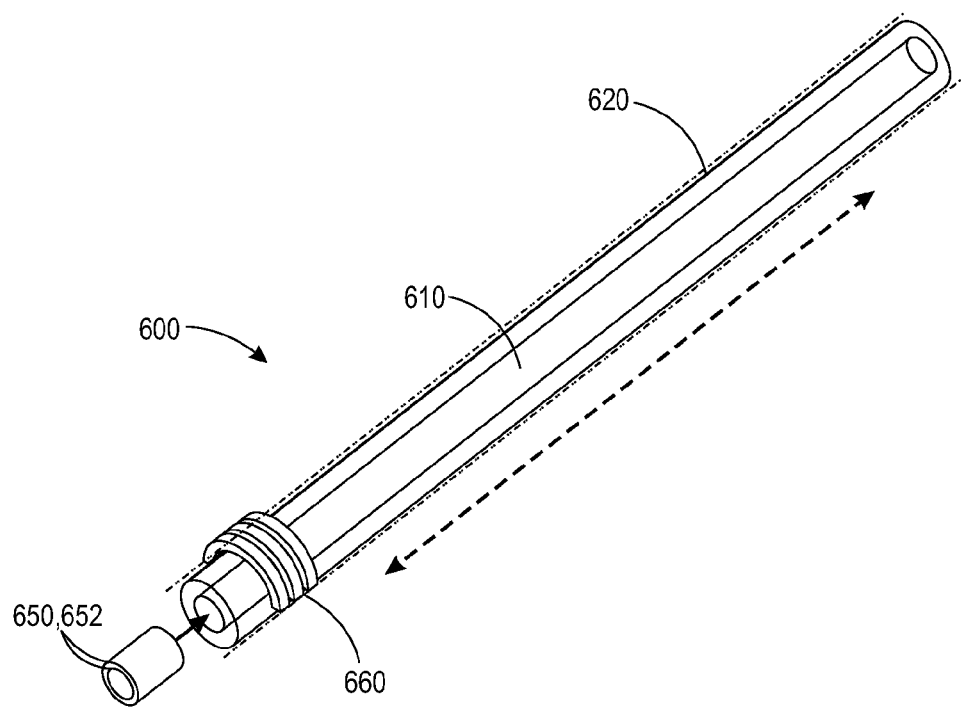
FIG. 7B is a perspective view of the embodiment of FIG. 7A

FIGS. 7A and 7B illustrates an exemplary embodiment of a system 600 with a cleaning device. The system 600 includes an inner compartment 612 separated from an outer compartment 622 by a membrane 610. The cleaning device includes an inner magnet brush 650 for cleaning an inner surface of the membrane 610 and an outer magnet brush 652 for cleaning an outer surface of the membrane 610. The system 600 further includes a transparent outer wall 620 and a traveling magnet 660 for engaging and spinning the magnet brushes 650, 652. In some embodiments, the traveling magnet 660 is powered by solar energy.

Figure 17A:
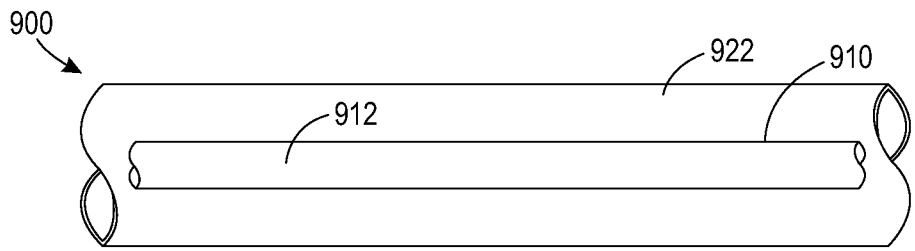
FIGS. 17A-C are perspective views of three exemplary reactor modules of the present disclosure.
Figure 17B:
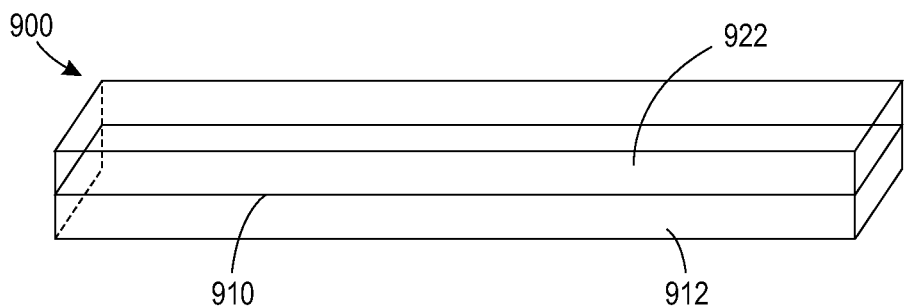
Figure 17C:
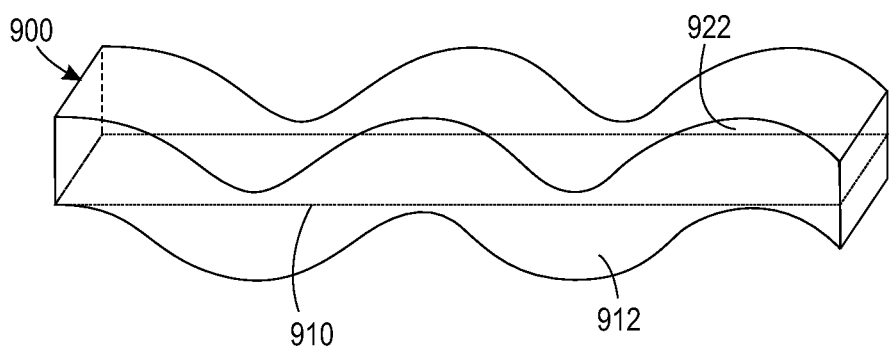

FIGS. 17A-C illustrate three non-limiting examples of reactor modules 900. Each reactor module includes a membrane 910 extending between a heterotrophic bioreactor 912 and an autotrophic bioreactor 922. In FIG. 17A, the module 900 has a substantially cylindrical configuration. In FIG. 17B, the module 900 has a panel-type configuration. In FIG. 17C, the module 900 has a serpentine or undulating configuration, and is an example of how reactor geometry can be used to enhance transport back and forth across the membrane 910.

In wastewater treatment embodiments where the heterotrophic bioreactor contains activated sludge, and if the solids residence time in the heterotrophic bioreactor is sufficiently long, the slow-growing, aerobic, autotrophic nitrifying bacteria (*Nitrosomonas* and *Nitrobacter*) will proliferate as part of the activated sludge community and nitrification can be accomplished. Depending on the influent nitrogen load (as total Kjedahl Nitrogen (TKN) and/or ammonia), the oxygen demand exerted by nitrifying organisms to accomplish nitrification is as high as 40% of the total oxygen demand of a wastewater treatment system. A benefit of operating the heterotrophic bioreactor side of the system at a longer solids residence time is that more endogenous respiration of activated sludge will occur, producing more carbon dioxide that can then be used to drive algal growth. Typical solids residence times used for the design of nitrifying activated sludge processes for treating domestic wastewater in the United States might range from 7 to 14 days when considering the mass of solids in aerated bioreactors maintained at temperatures as low as 15 to 8 degrees C., respectively. This is usually sufficient for preventing the washout of nitrifying organisms at the wastewater temperatures seen in the US in the winter. Operating SRTs needed to maintain nitrification are lower in winter seasons and colder climates.

At night, algae are inactive (when the light source is the sun) and oxygen is not produced. During this time, denitrification can be accomplished in embodiments for wastewater treatment where the heterotrophic bioreactor contains activated sludge. The ammonia that is not assimilated for growth of either bacteria or algae is oxidized to nitrate (nitrification), which is an electron acceptor that is used in place of oxygen for carbon oxidation when there is no oxygen present. Therefore, the diurnal cycling will produce alternating periods of aerobic and anoxic conditions, providing continuous carbon oxidation and alternating nitrification and denitrification sufficient to meet treatment objectives and discharge requirements.

Preliminary estimates suggest that, stoichiometrically, algal growth on the carbon dioxide released during heterotrophic wastewater treatment will be carbon-limited, and there will be an excess of oxygen produced during photosynthesis. The oxygen that remains after use during heterotrophic, aerobic carbon oxidation will be less than in conventional algal photobioreactors. In some embodiments, heterotrophic carbon oxidation in the heterotrophic bioreactor will mitigate oxygen toxicity for algae in the autotrophic bioreactor.

Figure 8:
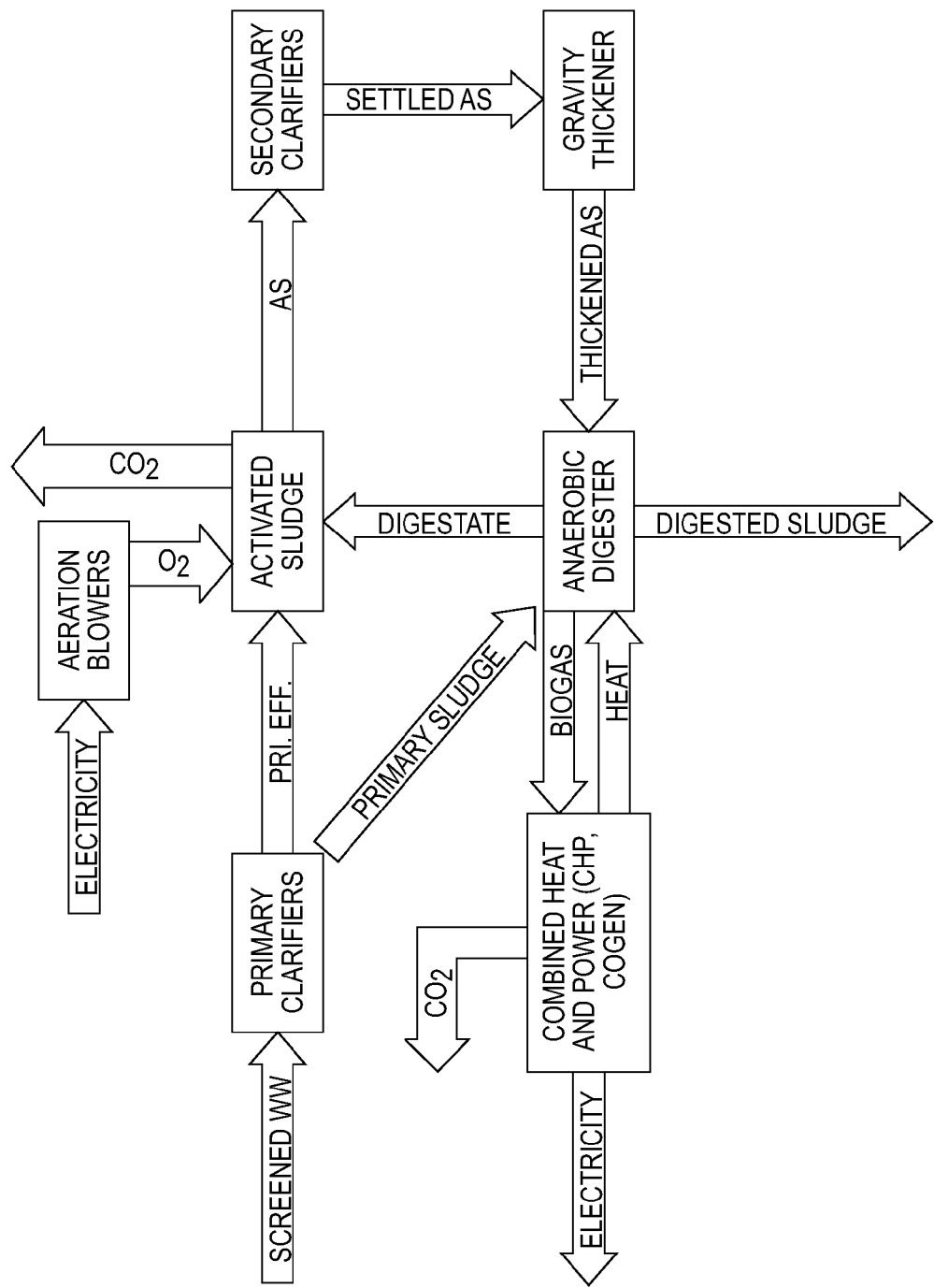
FIG. 8 is a process flow diagram for a conventional wastewater treatment facility.

FIG. 8 is a process flow diagram for a typical wastewater treatment facility. Even efficient facilities with anaerobic digesters and cogeneration/combined heat and power facilities (CHP) might only offset energy requirements by 50%.

Energy to supply air via blowers may constitute 60% of the electrical demand of the facility.

Figure 9:
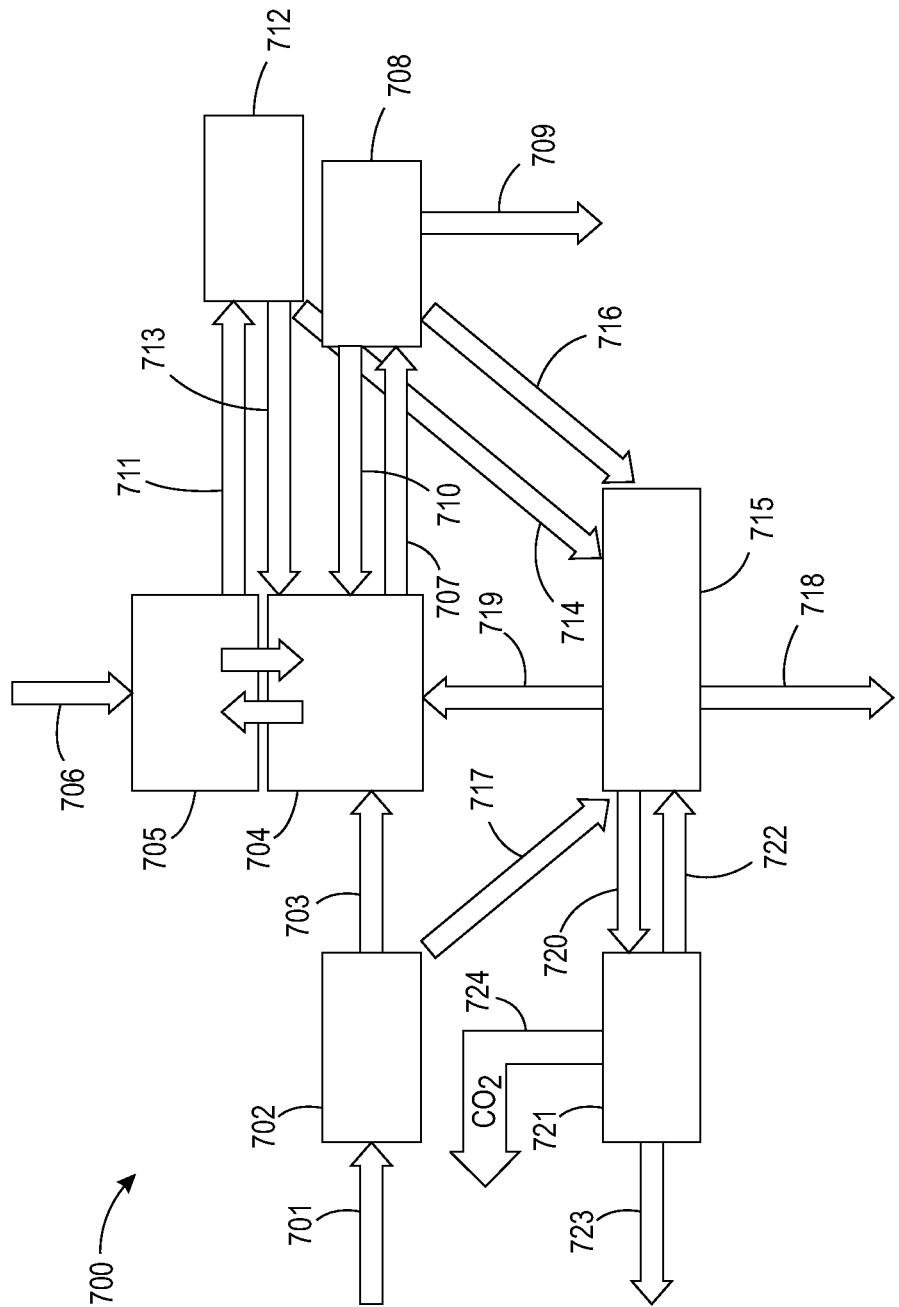
FIG. 9 is a process flow diagram for an exemplary embodiment of a wastewater treatment method of the present disclosure.
Figure 10:
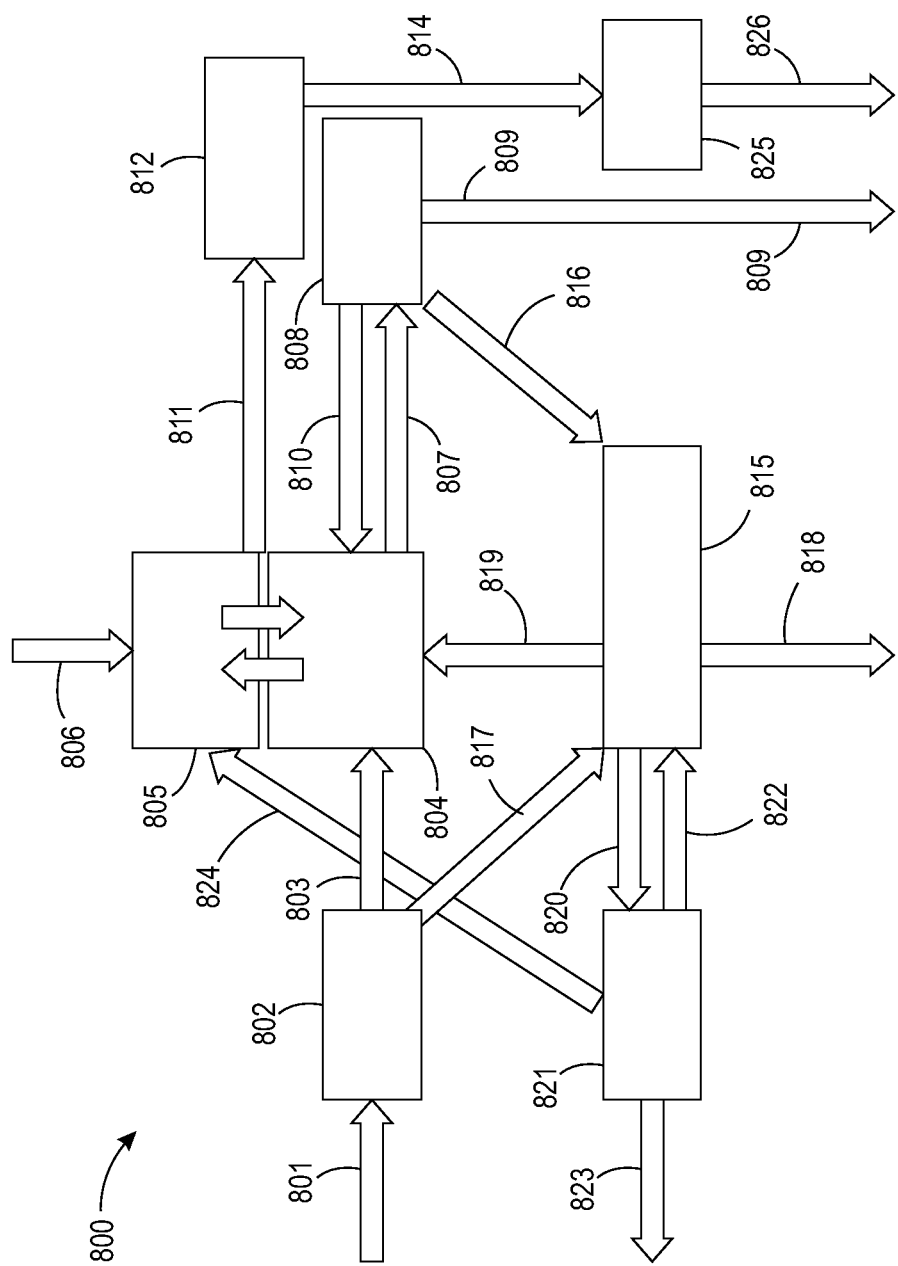
FIG. 10 is a process flow diagram for another exemplary embodiment of a wastewater treatment method of the present disclosure.

FIGS. 9 and 10 are process flow diagrams for embodiments of systems and methods of an embodiment for wastewater treatment where the heterotrophic bioreactor contains activated sludge and the autotrophic bioreactor contains algae. The systems and methods include the membrane-separated heterotrophic and autotrophic bioreactors described above. In addition to this bioreactor configuration, the diagrams further include an algae dewatering system that takes excess algae mass from the autotrophic bioreactor and delivers it at an increased concentration to either the on-site anaerobic digester or to an off-site biofuel refinery. In FIG. 9, the excess algae is used for on-site heat and power generation. In FIG. 10, the excess algae is used for off-site biofuel production. FIG. 10 also includes carbon capture and the recycling of flue gas 824 to the autotrophic bioreactor as an inorganic carbon source for algal growth and improved nutrient removal.

In the process and system 700 of FIG. 9, screened wastewater 701 is fed to primary clarifiers 702. The primary clarifiers 702 provide a primary effluent 703 to a heterotrophic bioreactor 704. The heterotrophic bioreactor 704 is separated from an autotrophic bioreactor 705 by a membrane such that carbon dioxide and nutrients may pass from the heterotrophic bioreactor 704 to the autotrophic bioreactor 705 and oxygen may pass from the autotrophic bioreactor 705 to the heterotrophic bioreactor 704. Light (e.g., sunlight) 706 passes through a transparent wall of the autotrophic bioreactor 705 to enable photosynthesis. The heterotrophic biomass 707 is fed to a final membrane 708 and a treated effluent 709 is produced. A final membrane return stream 710 is also produced and recycled to the heterotrophic bioreactor 704. Excess autotrophic biomass 711 from the autotrophic bioreactor 705 may be first provided to a thickening stage 712, or may flow directly to an anaerobic digester stage 715 (arrow not shown). From the thickening stage 712, a supernatant stream 713 may be recycled to the reactor stage and a thickened stream 714 may be provided to an anaerobic digester stage 715. Excess heterotrophic biomass 716 may also be provided to the digester stage 715 from the final membrane 708. Additionally, primary sludge 717 from the primary clarifiers may be provided to the anaerobic digester 715. Digested sludge 718 may be recovered from the anaerobic digester for land application/fertilizer. Digestate 719 may be provided to the activated sludge bioreactor 704. Biogas 720 generated in the anaerobic digester 715 can be provided to a combined heat and power cogeneration stage 721. The cogeneration stage 721 generates heat 722, electricity 723, and carbon dioxide 724. The heat 722 may be used on-site (e.g., for pre-heating the anaerobic digester 715 or the current embodiment (704 and 705 (arrow not shown)).

In the process and system 800 of FIG. 10, screened wastewater 801 is provided to primary clarifiers 802. A primary effluent 803 from the primary clarifiers 802 is provided to a heterotrophic bioreactor 804. Primary sludge 817 from the primary clarifiers may be provided to an anaerobic digester 815. The heterotrophic bioreactor 804 is separated from an autotrophic bioreactor 805 by a membrane such that carbon dioxide and nutrients may pass from the heterotrophic bioreactor 804 to the autotrophic bioreactor 805 and oxygen may pass from the autotrophic bioreactor 805 to the heterotrophic bioreactor 804. Light (e.g., sunlight) 806 is provided through a transparent wall of the autotrophic bioreactor 805 to enable photosynthesis. Excess autotrophic biomass 811 produced in the autotrophic bioreactor 805 may be provided to a thickening stage 812. A thickened autotrophic biomass 814 produced therein may be provided to an on-site or off-site biofuel refinery 825 to produce a biofuel 826. The heterotrophic biomass 807 may be provided to a final membrane 808 to produce a treated effluent 809. A final membrane return stream 810 is also produced and recycled to the heterotrophic bioreactor 804. Excess heterotrophic biomass 816 may also be provided to the digester stage 815 from the final membrane 808. The anaerobic digester 815 may produce a digested sludge 818 which may be used for land application/fertilizer, a digestate 819 which may be recycled to the reactor stage, and a biogas 820 which may be provided to a combined heat and power cogeneration stage 821. The cogeneration stage 821 may produce electricity 823, heat 822 which may be provided to the system 815 (e.g., for pre-heating the anaerobic digester), and carbon dioxide 824 which may be provided to the autotrophic bioreactor 805.

Figure 18:
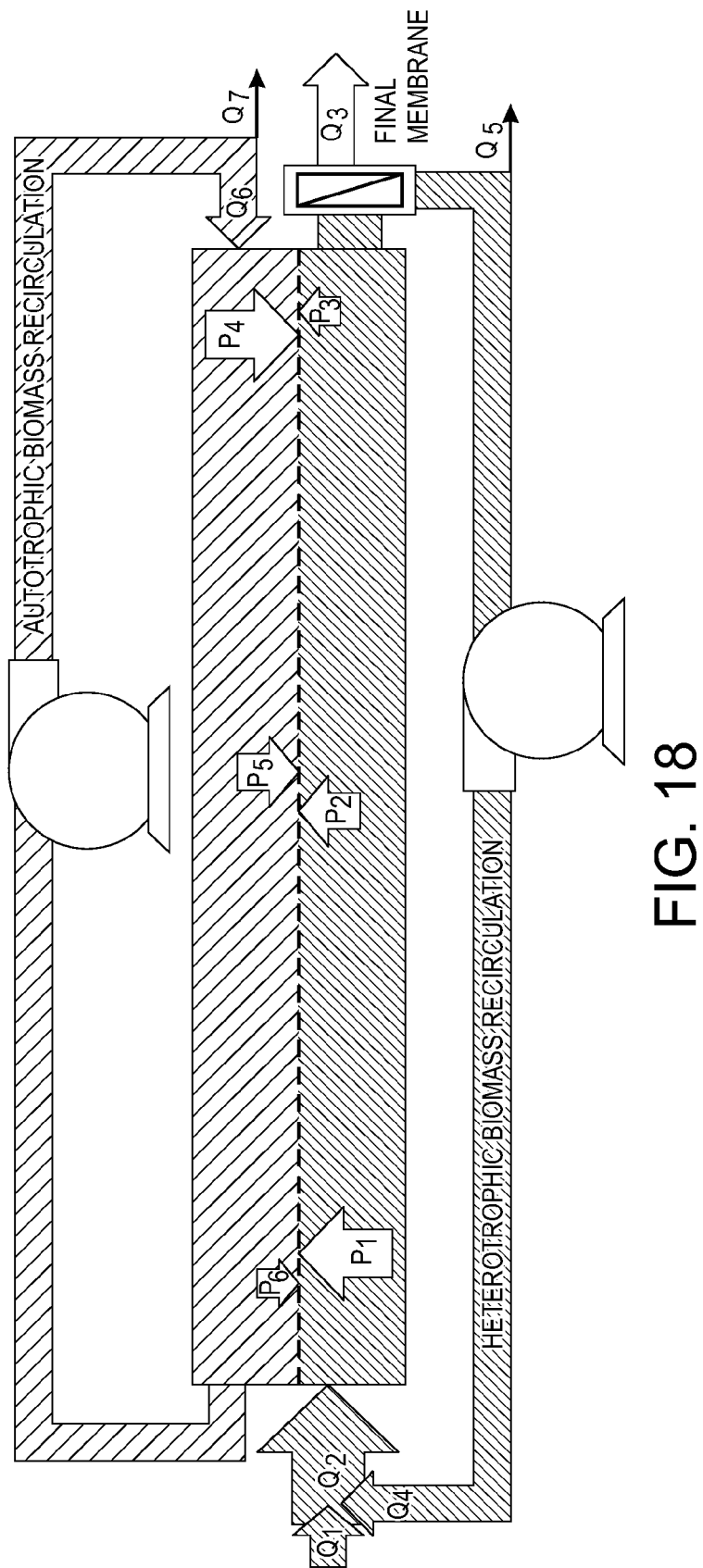
FIG. 18 is a schematic view of an exemplary system and method for treating wastewater according to some embodiments of the present disclosure.

In the process and system of 900 of FIG. 18 for an embodiment intended for wastewater treatment, which shows the relative magnitudes of pressure and flow with corresponding arrow thickness, primary effluent Q1 joins recycled heterotrophic biomass Q4 and enters the heterotrophic bioreactor. Autotrophic biomass is recirculated through the autotrophic bioreactor at an equivalent but counter current flow rate Q6. The resulting pressure drops (notably P1-P6 and P3-P4) drive flow across the membrane in opposite directions, from high pressure areas to low pressure areas. Excess autotrophic biomass Q7 and excess heterotrophic biomass Q5 are removed from the system and sent to an anaerobic digester. Clean effluent Q3 is discharged from the final membrane.

Where the influent wastewater flow rate is Q, the autotrophic and heterotrophic recycle rates may be in the range of from about 0.5 Q to about 5 Q, including about 1.5 Q. In some embodiments, Q is between 1,000 to 100,000,000 gallons per day.

Figure 11:
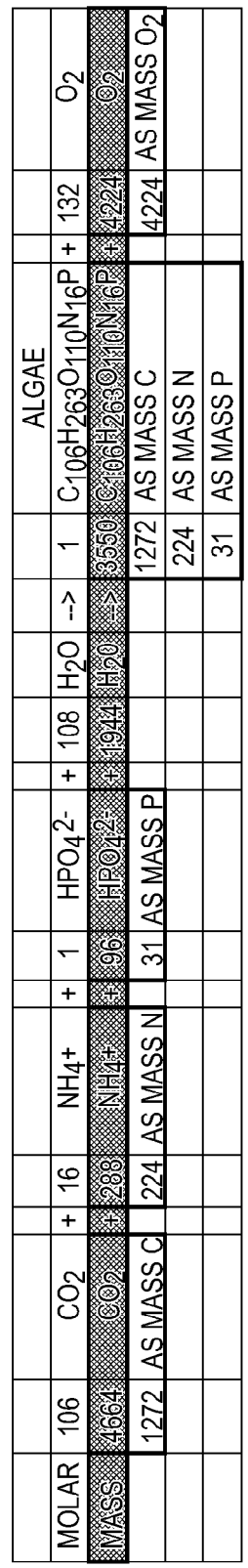

Calculations were performed as a proof of concept exercise for a wastewater treatment embodiment, where the autotrophic bioreactor contained photosynthetic algae and the heterotrophic bioreactor contained activated sludge. Mass balances for carbon, nitrogen, and phosphorous were determined using published bacterial and algal kinetic and stoichiometric values while incorporating standard process engineering design equations to establish proof of concept by designing a hypothetical wastewater treatment facility using a system of the present disclosure. FIG. 11 shows the stoichiometric relationship for algal growth. FIG. 12 shows the stoichiometric relationship for activated sludge (bacterial) growth. The balanced equations were converted to masses based on molecular weights. FIG. 13 shows the wastewater characteristics from a hypothetical town the size of Menlo Park, Calif. The city of Menlo Park produces about 10,000 $m^3$ per day of wastewater, or about 2.65 million gallons per day (mgd), and is used for the example system.

The tables below first present calculations for determining the oxidation of influent carbon and production of carbon dioxide, the amount of nitrogen and phosphorous used in the synthesis of bacterial cells, and the amount of oxygen required. Next, the amount of algae produced is calculated based on the quantity of carbon dioxide from the previous step, assuming that photosynthesis would only occur for about 6 hours per day. The amount of nitrogen and phosphorous used in the synthesis of algal cells is also calculated. Then, the quantity of oxygen generated from photosynthesis is determined. This is compared to the sum of the oxygen required for carbon oxidation and nitrification, and determined to be more than sufficient.

Part A: Design System for Heterotrophic Bioreactor Constants

| Kinetic Parameter | Value |
|---|---|
| Synthesis yield (biomass C:substrate C), Y | 0.64 |
| Molar ratio of C in bacteria biomass | 0.53 |
| Max growth rate, /day, $\mu_{max}$ | 3.2 |
| Endogenous decay (g-C/g-C*day), $k_d$ | 0.1 |

Step 1. Calculate Washout SRT for Heterotrophic Bioreactor $$\frac{1}{SRT_{min}} \approx \mu_{max} - k_d$$

| Parameter | Value | Unit |
|---|---|---|
| Washout Solids residence time | 0.323 | Days |
| Safety factor | 2.5 | |
| Design Solids residence time | 10.0 | Days |
| Design Activated sludge biomass concentration, as VSS | 7000 | mg/L VSS |
| Design Activated sludge biomass concentration, as C | 3716 | mg/L-C |
| Design Activated sludge biomass concentration, as TSS | 10000 | mg/L TSS |

Step 2. Calculate Volume of Heterotrophic Bioreactor $$V = \left(\frac{Q}{X}\right)\frac{Y \times SRT \times (S_i - S_e)}{1 + k_d \times SRT}$$

| Parameter | Value | Unit |
|---|---|---|
| Flow, Q | 10000 | m³/day |
| Substrate carbon, S | 118 | mg/L as C |
| Total reactor volume needed, V | 1008 | m³ |

Step 3. Calculate Excess heterotrophic biomass Production $$P_X = \frac{X \times V}{SRT}$$

| Parameter | Value | Unit |
|---|---|---|
| Excess Activated sludge biomass production, as kg-C, $P_X$ | 375 | kg C/day |
| Excess Activated sludge biomass production, as m³/day | 101 | m³/day |

Part B. Design System for Autotrophic Bioreactor Constants

| Kinetic Parameter | Value | Comment |
|---|---|---|
| Synthesis yield (biomass C:substrate C), Y | 1.00 | Volume calculation uses units of C |
| Molar ratio of C in algal biomass | 0.36 | |
| Max growth rate, /day, $\mu_{max}$ | 1.74 | |
| Decay, g-C/g-C*day, $k_d$ | 0.0684 | |

Step 4. Calculate Washout SRT for Autotrophic Bioreactor $$\frac{1}{SRT_{min}} \approx \mu_{max} - k_d$$

| Parameter | Value | Unit | Comment |
|---|---|---|---|
| Washout Solids residence time | 0.6 | Days | |
| Light availability factor | 0.25 | % of hours per day | Assuming only 6 hours of usable daylight |
| Design Solids residence time | 6.0 | Days | |
| Design algal biomass concentration | 2000 | mg/L VSS | |
| Design algal biomass concentration, as C | 717 | mg/L C | Volume calculation uses units of C |

Step 5. Calculate Volume of Autotrophic Bioreactor $$V = \left(\frac{Q}{X}\right)\frac{Y \times SRT \times (S_i - S_e)}{1 + k_d \times SRT}$$

| Parameter | Value | Unit |
|---|---|---|
| Flow, Q | 10000 | m³/day |
| Substrate (carbon) concentration, S | 66 | mg/L C |
| Total reactor volume needed, V | 1944 | m³ |

Step 6. Calculate Excess Algal Production $$P_X = \frac{X \times V}{SRT}$$

| Parameter | Value | Unit |
|---|---|---|
| Excess algal biomass production, as m³/day | 325 | m³/day |
| Algal biomass production, as kg-C, $P_X$ | 466 | kg C/day |
| Algal biomass production per unit autotrophic bioreactor surface area | 134 | g/m²/day |

Step 7. Calculate $CO_2$, $O_2$, N, P for Algal System and Bacterial System

| Parameter | Value | Unit | Comments |
|---|---|---|---|
| CO2—C produced by activated sludge biomass | 657 | kg-C | |
| CO2—C assimilated by algal biomass | 645 | kg-C | In the 6 hours of photosynthetic activity |
| C balance | 12 | kg-C | |
| C deficit? | No | | |
| O2 produced by algal biomass | 2179 | kg-$O_2$ | In the 6 hours of photosynthetic activity |
| O2 needed for nitrification | 701 | kg-$O_2$ | 4.5 kg $O_2$ per kg $NH_4$—N |
| O2 needed for carbon oxidation | 1180 | kg-$O_2$ | |
| O2 balance | 298 | kg-$O_2$ | |
| O2 deficit? | No | | |
| Total N available | 300 | kg-N | |
| N needed for bacterial growth | 62 | kg-N | |
| N needed for algal growth | 82 | kg-N | |
| remaining NH4—N requiring nitrification | 156 | kg-N | |
| N balance | 156 | kg-N | |
| N deficit? | No | | |
| Nitrate-N available for carbon oxidation at night | 15.6 | mg/L-N | (denitrification of nitrate-N to nitrogen gas) |
| P available | 80 | kg-P | |
| P needed for bacterial growth | 8 | kg-P | |
| P needed for algal growth | 11 | kg-P | |
| P balance | 61 | kg-P | |
| P deficit? | No | | |
| effluent phosphorus, mg/L | 2.1 | mg/L P | Assuming 50% of P from primary effluent is particulate and captured by final membrane |

Step 8. Process Sizing, Tube Within a Tube Embodiment

| Parameter | Value | Unit | Comments |
|---|---|---|---|
| heterotrophic bioreactor (membrane) volume | 1008 | $m^3$ | |
| heterotrophic bioreactor (membrane) diameter | 0.15 | m | |
| Heterotrophic bioreactor (membrane) surface area | 26,891 | $m^2$ | |
| autotrophic bioreactor (outer tube) volume | 3888 | $m^3$ | |
| autotrophic bioreactor (outer tube) diameter | 0.33 | m | |
| autotrophic bioreactor (outer tube) surface area | 58,780 | $m^2$ | |
| Total length of system | 57,532 | m | |
| Hydraulic residence time | 11.8 | Hours | |
| Module length | 2 | M | |
| # of modules | 28,532 | # | |
| # of parallel legs | 17 | # | |
| Velocity per leg | 0.05 | m/s | |
| Headloss through heterotrophic bioreactor system | 0.71 | psi | |
| Headloss through autotrophic bioreactor system | 1.42 | psi | |
| Stack height | 5 | # | Bioreactors in a vertical stack |
| Additional process footprint | 50% | % | for space between and around stacks of bioreactors |
| Total footprint | 5613 | $m^2$ | |
| Footprint per unit volume treated | 0.56 | $m^2/m^3$ | For the current embodiment downstream of a primary clarifier |
| Typical footprint per unit volume treated | 0.128 | $m^2/m^3$ | For bioreactors and clarifiers downstream of a primary clarifier |
| Size relationship | 4.4 | | Times more footprint than conventional secondary treatment |

The quantity of excess heterotrophic biomass is calculated based on a solids residence time that ensured complete nitrification at 10 degrees Celsius. Then, the power generated from the anaerobic digestion of primary sludge, excess autotrophic biomass, and excess heterotrophic biomass is calculated as shown in FIG. 15, along with conservatively estimated power requirements to supply pumping for the proposed system. FIG. 16 compares power requirements per process for a plant with an exemplary embodiment of the present disclosure and a conventional plant.

For embodiments intended for wastewater treatment where the heterotrophic bioreactor contains activated sludge and the autotrophic bioreactor contains photosynthetic algae, the algae can be anaerobically digested to produce methane, albeit at a reduced yield (roughly 10-30% less on a L $CH_4$ produced/kg VSS algae digested basis) compared to excess activated sludge or primary solids collected from wastewater treatment facilities. The quantity of algae produced (and hence biogas production potential) will be significant and beneficial. The example exercise suggests that nearly as much algal mass can be generated as is typically recovered from primary solids and excess activated sludge on a per unit wastewater basis. This would result in about 80% more biogas being produced from the disclosed systems and processes when compared to a conventional wastewater treatment process.

With today's economic and technical limitations, anaerobic digestion and CHP processes are cost-effective at larger wastewater treatment plants (theoretically as low as 1 mgd in capacity but typically greater than 5 mgd in capacity). Existing facilities may be able to readily accommodate algal biomass via co-digestion. Increasing (perhaps to 3-4 kWh/$m^3$)) the potential energy production per unit of wastewater treated by adding algae biomass in digesters will lower the treatment facility capacity break-point at which anaerobic digestion followed by CHP becomes cost effective (e.g., from 1 mgd to 0.5 mgd), expanding the digester/CHP market.

Using algal biomass harvested from the disclosed systems and methods for co-digestion in existing anaerobic digesters for CHP production rather than biofuel production, at least at first, may be the most streamlined and efficient approach for maximizing the benefits of algae grown on wastewater, as current economic analyses have indicated that small scale production and decentralized biofuel production using algal biomass are not cost effective. The additional organic loads to digesters results in more biogas that can be used for heat to ensure stable operation during winters for cold climates—either as heated reactors or enclosures for reactors (greenhouses), for example.

The proposed dual compartment bioreactor system that allows for the ideal symbiosis of heterotrophic and autotrophic populations separated by a shared membrane in a closed system yields advantages for both wastewater treatment and algal production.

Aspects for wastewater treatment in accordance with the present teachings include:
  reduced or eliminated need for oxygen supplementation for removal of organic matter from waste water;
  reduced nutrients (e.g., nitrogen and phosphorous) from effluents discharged to receiving waters;
  reduced metals (e.g., chromium, copper, and zinc) from effluents discharged into receiving waters;
  reduced energy use, production of energy to offset energy use for treatment, or production of more energy than is needed for treatment;
  reduced or eliminated supplemental oxygen need for nitrification of ammonia in wastewater;
  reduced or eliminated release of greenhouse gases through heterotrophic respiration; and
  increase biogas production per unit volume of wastewater treated.

Aspects for algal production in accordance with the present teachings include:
  reduced or eliminated need for carbon supplementation for autotrophic algal production;
  reduced or eliminated need for oxygen supplementation for heterotrophic algal production;
  reduce or eliminated need for nutrient supplementation for heterotrophic and autotrophic algal production, and
  reduced or eliminated toxic accumulation of oxygen.

It will be appreciated that variants of the above-disclosed and other features and functions, or alternatives thereof, may be combined into many other different systems or applications. Various presently unforeseen alternatives, modifications, variations or improvements therein may be subsequently made by those skilled in the art which are also intended to be encompassed by the following claims.

What is claimed is:

1. A dual compartment bioreactor system comprising:
  a first compartment containing heterotrophic organisms;
  a second compartment containing autotrophic organisms; and
  a membrane subsystem in operational contact with the first compartment and the second compartment;
  wherein the membrane subsystem is configured to permit transport of at least one of gases and solutes from the first compartment to the second compartment; and
  wherein the membrane subsystem comprises a liquid permeable integrated hydrophobic/hydrophilic membrane having hydrophobic regions which only allow for the transport of gases, and hydrophilic regions which allow for the transport of fluids, solutes, and gases.

2. The dual compartment bioreactor system of claim 1, wherein the second compartment comprises a transparent outer wall that allows passage of visible light.

3. The dual compartment bioreactor system of claim 1, further comprising:
  a magnetic cleaner configured to clean at least one surface of at least one membrane of the membrane subsystem.

4. The dual compartment bioreactor system of claim 1, wherein the membrane subsystem consists of the liquid permeable membrane; and wherein the membrane is in physical contact with the first compartment and the second compartment.

5. The dual compartment bioreactor system of claim 1, wherein the second compartment circumferentially surrounds the first compartment.

6. The dual compartment bioreactor system of claim 1, further comprising:
  a magnetic cleaner configured to clean one or more surfaces of one or more membranes of the membrane subsystem.

7. The dual compartment bioreactor system of claim 6, wherein the magnetic cleaner comprises:
  an electromagnet mounted on an external surface of a transparent outer wall of the second compartment; and
  a magnetic brush mounted on at least one of an internal surface of the first compartment, an internal surface of the second compartment; and a surface of a membrane of the membrane subsystem.

8. A method of metabolizing inputs using the dual compartment bioreactor system of claim 1, the method comprising:
providing inputs to the first compartment;
metabolizing the inputs and growing heterotrophic organisms in the first compartment;
recovering a component from the first compartment or the second compartment; and
metabolizing the inputs and growing autotrophic organisms in the second compartment;
wherein the second compartment comprises a transparent outer wall.

9. The method of claim 8, wherein the membrane subsystem consists of the liquid permeable membrane; wherein the membrane circumferentially surrounds at least a first portion of the first compartment; and wherein the second compartment circumferentially surrounds at least a second portion of the membrane.

10. The method of claim 8, wherein the membrane subsystem consists of the liquid permeable membrane; and wherein the membrane is in direct contact with the first compartment and the second compartment.

11. The method of claim 8, further comprising:
cleaning a membrane of the membrane subsystem by moving a magnet along the transparent outer wall;
wherein a first magnetic brush is configured to clean at least one surface of the membrane.

12. The method of claim 8, further comprising:
continuously recirculating autotrophic biomass of the second compartment in a countercurrent direction to recirculating heterotrophic biomass of the first compartment.

13. The method of claim 12, further comprising:
removing excess autotrophic biomass from the second compartment; and
removing excess heterotrophic biomass from the first compartment.

14. The method of claim 8, further comprising:
creating pressure differences to control transport across one or more membranes of the membrane system.

15. The method of claim 8, wherein the membrane system comprises an integrated hydrophilic/hydrophobic membrane.

16. The method of claim 8, further comprising:
monitoring photosynthetic activity by autotrophic organisms by measuring a residual dissolved oxygen concentration in at least one of the first compartment and the second compartment;
optionally supplying supplemental oxygen to the first compartment when photosynthetic activity is low;
monitoring respiration activity by measuring the residual dissolved carbon dioxide concentration in at least one of the first compartment and the second compartment; and
optionally supplying supplemental carbon dioxide to the second compartment when respiration activity is low.

17. The method of claim 8, wherein the inputs comprise waste organic substrates and waste nutrients; and wherein the method treats wastewater.

18. The method of claim 8, wherein the inputs comprise manufactured organic substrates and manufactured nutrients; and wherein the method produces algae.

19. A dual compartment bioreactor system comprising:
a first compartment containing heterotrophic organisms;
a second compartment containing autotrophic organisms; and
a membrane subsystem in operational contact with the first compartment and the second compartment;
wherein the membrane subsystem is configured to permit transport of at least one of gases and solutes from the first compartment to the second compartment;
wherein the membrane subsystem is configured to permit transport of at least one of gases and solutes from the second compartment to the first compartment;
wherein the membrane subsystem consists of one membrane having hydrophobic regions which only allow for the transport of gases, and hydrophilic regions which allow for the transport of fluids, solutes, and gases;
wherein the membrane is in direct contact with the first compartment and the second compartment; and
wherein the system has a serpentine configuration.

* * * * *